(12) United States Patent
Hur et al.

(10) Patent No.: US 9,574,978 B2
(45) Date of Patent: Feb. 21, 2017

(54) SAMPLER

(75) Inventors: Dae-Sung Hur, Seoul (KR); Ji-Young Park, Seoul (KR)

(73) Assignee: NANOENTEK, INC., Seoul (KR)

( * ) Notice: Subject to any disclaimer, the term of this patent is extended or adjusted under 35 U.S.C. 154(b) by 122 days.

(21) Appl. No.: 13/990,965

(22) PCT Filed: Dec. 1, 2011

(86) PCT No.: PCT/KR2011/009258
§ 371 (c)(1),
(2), (4) Date: May 31, 2013

(87) PCT Pub. No.: WO2012/074308
PCT Pub. Date: Jun. 7, 2012

(65) Prior Publication Data
US 2013/0243665 A1   Sep. 19, 2013

(30) Foreign Application Priority Data

Dec. 3, 2010   (KR) .................. 10-2010-0123045
Mar. 21, 2011   (KR) .................. 10-2011-0024921

(51) Int. Cl.
*G01N 1/38*     (2006.01)
*B01L 3/02*     (2006.01)
(Continued)

(52) U.S. Cl.
CPC .............. *G01N 1/38* (2013.01); *B01L 3/0248* (2013.01); *B01L 3/502* (2013.01); *A61B 5/14* (2013.01);
(Continued)

(58) Field of Classification Search
CPC ... A61B 5/150389; A61B 5/1405; A61B 5/14; A61B 5/150633; A61M 2005/3106; A61M 39/04; A61M 39/14; A61M 5/162; A61M 5/24; B01L 2300/044; A61J 1/2096; A61J 1/1406; A61J 1/2089; A61J 2001/2013; C12M 33/04
(Continued)

(56) References Cited

U.S. PATENT DOCUMENTS 2,724,383 A * 11/1955 Lockhart ............... A61J 1/2089
                                                    604/204
3,585,984 A *  6/1971 Buchanan ..................... 600/577
(Continued)

FOREIGN PATENT DOCUMENTS

JP       09-0 61425 A    3/1997
JP       10-170510 A     6/1998
KR    10-2006-0005390 A  1/2006

*Primary Examiner* — Lyle Alexander
*Assistant Examiner* — Bryan Kilpatrick
(74) *Attorney, Agent, or Firm* — Paratus Law Group, PLLC

(57) ABSTRACT

Disclosed therein is a sampler. The sampler includes: a chamber accommodating a fluid or solid reagent therein and being sealed at both ends with penetrable films; a tube joined with the chamber at one side, the tube having a hollow portion therein; and a movable bar having a tip which is formed at one end and has a specimen extracting portion, the tip being guided and moved through a hollow portion, the tip being adapted for mixing the specimen extracted by the specimen extracting portion with the reagent so as to form a diluted solution while penetrating through one end of the chamber and adapted for quantitatively discharging out the diluted solution while penetrating through the other end of the chamber.

8 Claims, 31 Drawing Sheets

(51) Int. Cl.
*B01L 3/00* (2006.01)
*A61B 5/145* (2006.01)

(52) U.S. Cl.
CPC ......... *B01L 3/563* (2013.01); *B01L 2200/0605* (2013.01); *B01L 2300/046* (2013.01); *B01L 2300/047* (2013.01); *B01L 2300/0672* (2013.01); *B01L 2300/0832* (2013.01); *B01L 2300/0838* (2013.01); *B01L 2400/0406* (2013.01); *B01L 2400/0683* (2013.01)

(58) Field of Classification Search
USPC .. 422/500, 944; 600/577; 604/86; 73/864.01
See application file for complete search history.

(56) References Cited

U.S. PATENT DOCUMENTS

| | | | | |
|---|---|---|---|---|
| 5,478,328 | A | * | 12/1995 | Silverman et al. ........... 604/272 |
| 5,602,037 | A | * | 2/1997 | Ostgaard et al. ............... 436/69 |
| 5,888,826 | A | * | 3/1999 | Ostgaard et al. ............... 436/69 |
| 2006/0199275 | A1 | | 9/2006 | Togawa et al. |

* cited by examiner ically discharge the
SAMPLER

CROSS REFERENCE TO PRIOR APPLICATION

This application is a National Stage Patent Application of PCT International Patent Application No. PCT/KR2011/009258 (filed on Dec. 1, 2011) under 35 U.S.C. §371, which claims priority to Korean Patent Application Nos. 10-2010-0123045 (filed on Dec. 3, 2010) and 10-2011-0024921 (filed on Mar. 21, 2011), which are all hereby incorporated by reference in their entirety.

BACKGROUND OF THE INVENTION

Field of the Invention

The present invention relates to a sampler, and more particularly, to a sampler which can mix a reagent with a specimen to form a diluted solution and can quantitatively discharge the diluted solution.

Background Art

In general, analysis of a fluid sample has been widely used not only in the fields of chemistry and biotechnology but also in the field of diagnosis through analysis of blood and body fluids extracted from a patient.

Recently, in order to analyze such a fluid sample more simply and effectively, compact-size analysis and diagnosis apparatuses of various kinds have been developed.

In the meantime, one of important things to analyze the fluid sample is to preprocess the fluid sample.

Here, preprocessing of the fluid sample means to extract a specimen of a wanted amount before analysis of the fluid sample and to exactly treat the extracted specimen at a proper ratio, for instance, using a dilution buffer, or to mix the specimen with a solid or liquid reagent, or to separate and refine the specimen utilizing a filler or a supporter.

For this, typically, the fluid sample is preprocessed using a pipette or a dropper. However, in the case of a sample analysis of a lab-on-a-chip or lab-on-a-tip unit, because the sample used for preprocessing is very small in quantity and must be processed very accurately, it is not easy to accurately preprocess a very small amount of the sample using the pipette or the dropper.

Moreover, in the field inspection method, the extracted sample is preprocessed, and then, inputted into a measuring device, but in the inputting step, there occurs an error in amount of the inputted sample.

Therefore, in handling the very small amount of blood or other sample, necessity of a sampler, which can minimize the error in handling a very small amount of blood or sample and make the handling process easy so that unskilled persons can use it after listening to a simple explanation, is on the rise.

SUMMARY OF THE INVENTION

Accordingly, the present invention has been made to solve the above-mentioned problems occurring in the prior arts, and it is an object of the present invention to provide a sampler which can preprocess, for instance, mix a previously measured fluid or solid reagent with a specimen to form a diluted solution and quantitatively discharge the diluted solution.

It is another object of the present invention to provide a sampler which can obtain a specimen of a fixed quantity using a capillary structure.

It is a further object of the present invention to provide a sampler which can dilute or mix the previously measured fluid or solid sample with the specimen at a certain ratio and at a certain concentration without other external measuring devices and external power.

It is a still further object of the present invention to provide a sampler which can be assembled in a one-touch manner and can carry out all processes just by one-direction manipulation without using many steps or two-way manipulation.

It is another object of the present invention to provide a sampler which can prevent the preprocessed sample from leaking out during a quantitative discharge process of the preprocessed sample so as to keep an experimental environment clean.

To accomplish the above objects, according to a first aspect of the present invention, there is provided a sampler comprising a chamber accommodating a fluid or solid reagent therein and being sealed at both ends with penetrable films; and a tip adapted for accommodating an extracted specimen therein, mixing the specimen with the reagent so as to form a reacted specimen while penetrating through one end of the chamber, and quantitatively discharging out the reacted specimen while penetrating through the other end of the chamber.

The tip comprises a specimen extracting portion for extracting the specimen.

The sampler further comprises a movable bar formed integrally with the tip to move the tip by steps.

The sampler further comprises a tube joined with the chamber at one side, the tube having a hollow portion therein.

The sampler further comprises a guide protrusion disposed at one side of the movable bar; and a guide hole disposed in the tube for guiding a movement of the guide protrusion so as to regulate the movement of the movable bar by steps.

The guide hole is formed to regulate a discharged volume of the reacted specimen by steps.

The chamber comprises at least one ring-shaped protrusion formed at one side of the chamber in a circumferential direction, so that the chamber and the tube are forcedly fit with each other.

The chamber and the tube are joined and combined with each other by a fitting protrusion formed on the chamber and a joining groove formed in the tube corresponding to the fitting protrusion.

The movable bar a pressing portion which quantitatively discharges the reacted specimen by applying a fixed pressure to the reacted specimen inside the chamber when a user presses the other end of the movable bar after the tip penetrates the other end of the chamber.

The tip comprises a discharge channel for discharging the reacted specimen to the end.

The tip further comprises a mixing hole which communicates with the specimen extracting portion and the discharge channel and has a space where the specimen extracted by the specimen extracting portion can be mixed with the reagent.

The reagent contains at least one of silica particles which facilitate extraction of DNA or RNA by applying a physical force to a blood sample, antibodies selectively separating protein, and reagents utilized as supporters.

The tip is tapered, and an outlet disposed at the other end of the chamber comprises an inclined portion being formed in correspondence with the shape of the tip and getting in contact with the tip.

To accomplish the above objects, according to a second aspect of the present invention, there is provided a sampler comprising a chamber accommodating a fluid or solid reagent therein and being sealed at both ends with penetrable films; a movable bar having a tip which is formed at one end and has a specimen extracting portion, the tip adapted for mixing the specimen extracted by the specimen extracting portion with the reagent so as to form a reacted specimen while penetrating through one end of the chamber and adapted for quantitatively discharging out the reacted specimen while penetrating through the other end of the chamber; and a tube for guiding a movement of the movable bar by steps.

The tip comprises a discharge channel for discharging the reacted specimen to the end.

The tip further comprises a mixing hole which communicates with the specimen extracting portion and the discharge channel and has a space where the specimen extracted by the specimen extracting portion can be mixed with the reagent.

The movable bar a pressing portion which quantitatively discharges the reacted specimen by applying a fixed pressure to the reacted specimen inside the chamber when a user presses the other end of the movable bar after the tip penetrates the other end of the chamber.

The reagent contains at least one of silica particles which facilitate extraction of DNA or RNA by applying a physical force to a blood sample, antibodies selectively separating protein, and reagents utilized as supporters.

The sampler further comprises a guide protrusion disposed at one side of the movable bar; and a guide hole disposed in the tube for guiding a movement of the guide protrusion so as to regulate the movement of the movable bar by steps.

The guide hole is formed to regulate a discharged volume of the reacted specimen by steps.

The chamber comprises at least one ring-shaped protrusion formed at one side of the chamber in a circumferential direction, so that the chamber and the tube are forcedly fit with each other.

The chamber and the tube are joined and combined with each other by a fitting protrusion formed on the chamber and a joining groove formed in the tube corresponding to the fitting protrusion.

The tip is tapered, and an outlet disposed at the other end of the chamber comprises an inclined portion being formed in correspondence with the shape of the tip and getting in contact with the tip.

To accomplish the above objects, according to a third aspect of the present invention, there is provided a sampler comprising a chamber accommodating a fluid or solid reagent therein and being sealed at both ends with penetrable films; a tube joined with the chamber at one side, the tube having a hollow portion therein; and a movable bar accommodating the extracted specimen, the movable bar mixing the specimen with the reagent so as to form a reacted specimen while being inserted into the chamber, wherein the reacted specimen is quantitatively discharged from the chamber while the movable bar penetrates through the other end of the chamber.

To accomplish the above objects, according to a fourth aspect of the present invention, there is provided a sampler comprising a chamber having a space for accommodating a fluid or solid reagent therein; a tip disposed inside the chamber, the tip having a discharge channel for discharging the specimen which is mixed and reacted with the reagent; and a cylinder for moving the tip, wherein the reacted specimen is quantitatively discharge from the chamber while the tip penetrates through the other end of the chamber.

The sampler further comprises a membrane for refining and discharging the reacted specimen.

The tip comprises at least one separation hole for separating wanted materials during a centrifugal process after the chamber is mounted on a centrifuge.

To accomplish the above objects, according to a fifth aspect of the present invention, there is provided a sampler comprising a tip having a specimen extracting portion formed at one end portion of the tip for accommodating an extracted specimen therein; and a chamber having a penetrable pouch disposed at one end portion and a penetrable discharge film formed at the other end portion so as to accommodate a fluid or solid reagent inside the chamber, wherein the reagent and the specimen are mixed together so as to form a reacted specimen while one end portion of the tip penetrates through the pouch and is inserted into the chamber, and the reacted specimen is quantitatively discharged out while the end portion of the tip presses a pressing portion after penetrating through the discharge film.

The sampler further comprises a discharge part being disposed at the other end portion of the chamber and having a discharge passage formed therein for quantitatively discharging the reacted specimen when the pressing portion is pressed in a state where the tip penetrating the discharge film is located in the discharge passage.

The discharge part is detachably joined to the other end portion of the chamber and is replaceable with a discharge part, which has a diameter of a discharge passage corresponding to a discharged volume of the reacted specimen.

The tip comprises a movable bar formed integrally, and the movable bar comprises a pressing plate to which an external force applied to make the tip penetrate through the discharge film is applied; a stopper caught to the other end portion of the chamber so as to stop a movement of the movable bar; and a pressurizing portion being moved in a state where the outer face is in contact with the inner face of the chamber when the movable bar is moved, so that one side of the inside of the chamber is sealed and the reacted specimen pressurized by the pressing portion is discharged to the discharge part.

The specimen extracting portion is formed in a longitudinal direction of the tip and is opened at both sides toward the outside of the tip.

The pressing portion is formed integrally with the outer face of the chamber in such a way as to be pressed by an external force so as to increase the inside pressure of the chamber.

The sampler further comprises a cap joined to the other end of the chamber for accommodating the reacted specimen leaking out by the inside pressure of the chamber when the other end of the chamber is penetrated.

The cap comprises at least one pressure discharge hole for decreasing pressure generated when the cap is joined with the chamber.

The cap comprises at least one protrusion formed at one side of the inner circumference thereof in the circumferential direction, so that the chamber and the cap are forcedly fit with each other.

The cap comprises: a hand-grip portion for allowing the user to grasp when the cap is assembled to or disassembled from the chamber; and at least one slip-preventing protrusion formed at the hand-grip part for preventing a slip.

The sampler according to the present invention can mix a previously measured fluid or solid reagent with a specimen so as to dilute or separate, and quantitatively discharge out the reacted specimen.

Moreover, the sampler can obtain a specimen of a fixed quantity using a capillary structure.

Furthermore, the sampler can dilute or mix the previously measured fluid or solid reagent with the specimen at a certain ratio and at a certain concentration without other external measuring devices and external power.

Additionally, the sampler can carry out all processes just by one-direction manipulation without using many steps or two-way manipulation.

In addition, the sampler can prevent the preprocessed sample from leaking out during the quantitative discharge process of the preprocessed sample so as to keep an experimental environment clean.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
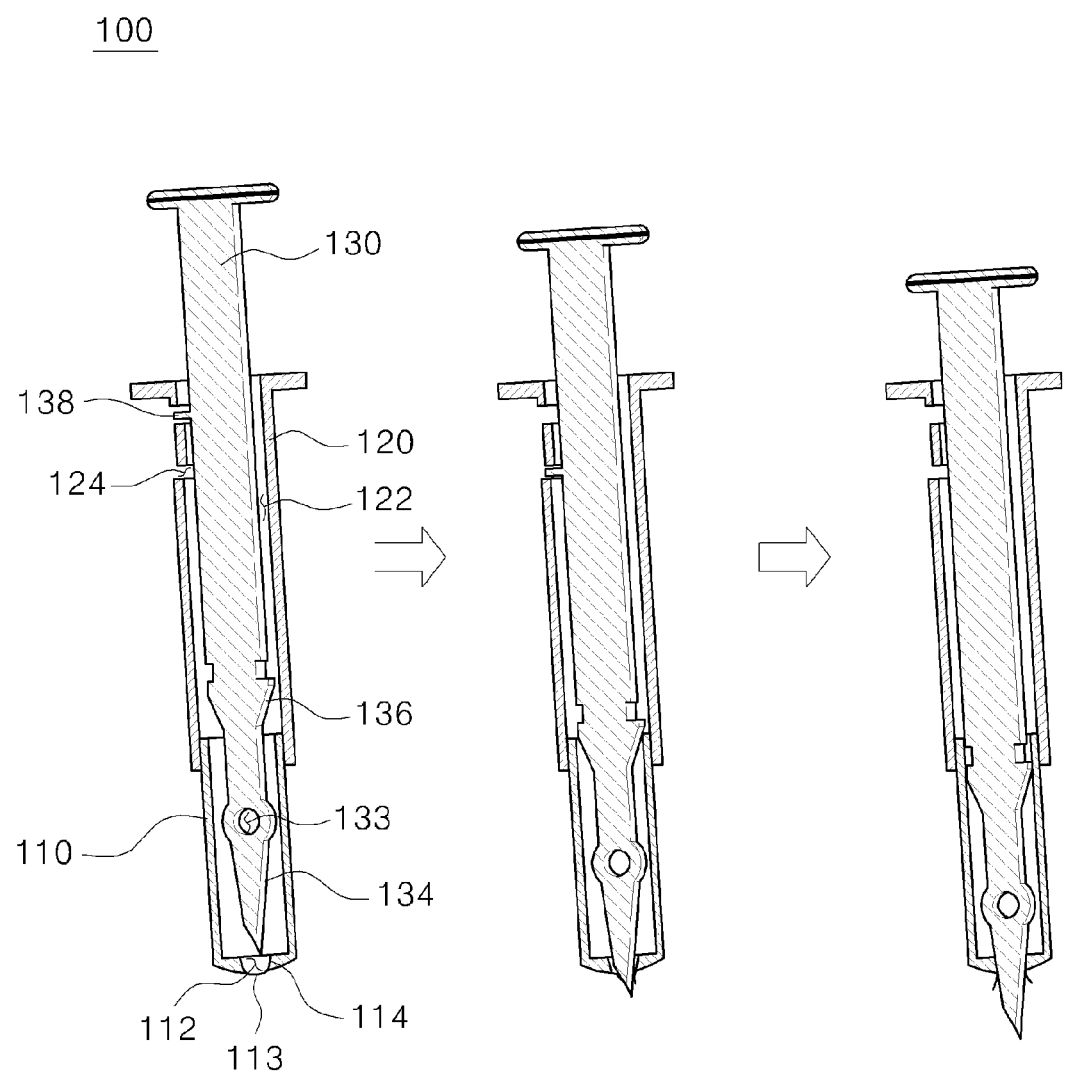
FIG. 1 is a sectional view showing an operational process of a sampler divided into three steps according to a first preferred embodiment of the present invention.

Reference will be now made in detail to the preferred embodiment of the present invention with reference to the attached drawings. However, the present invention is not restricted to the embodiments of the present invention but can be embodied in other various forms. The embodiments described in the present invention are provided in order to make the described contents thorough and perfect and to sufficiently transfer the technical idea of the present invention to those skilled in the art. The same reference numerals designate the same parts in the present invention.

Figure 2:
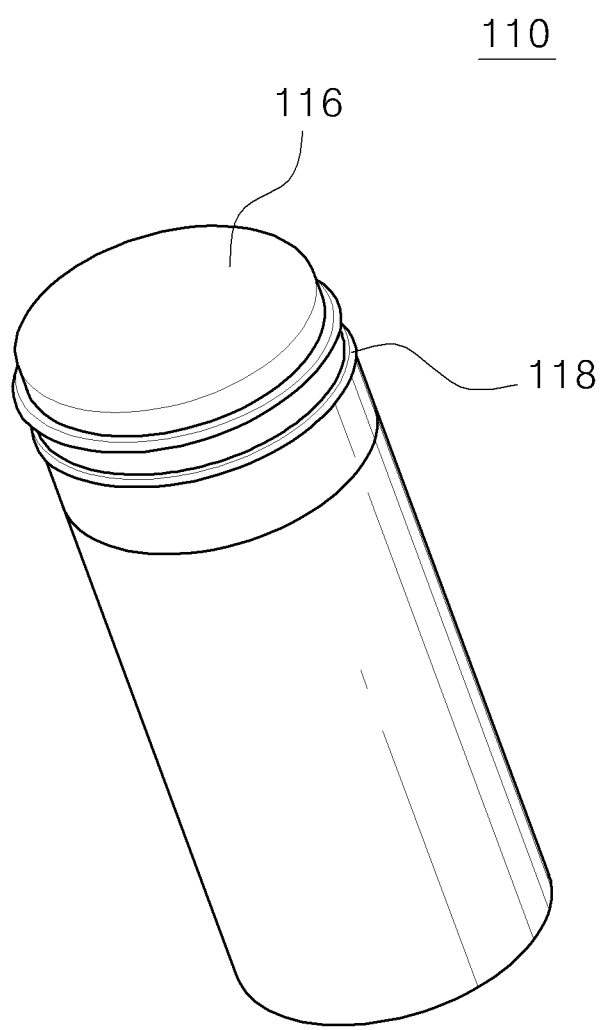
FIG. 2 is a perspective view of a chamber of the sampler according to the first preferred embodiment of the present invention.
Figure 3:
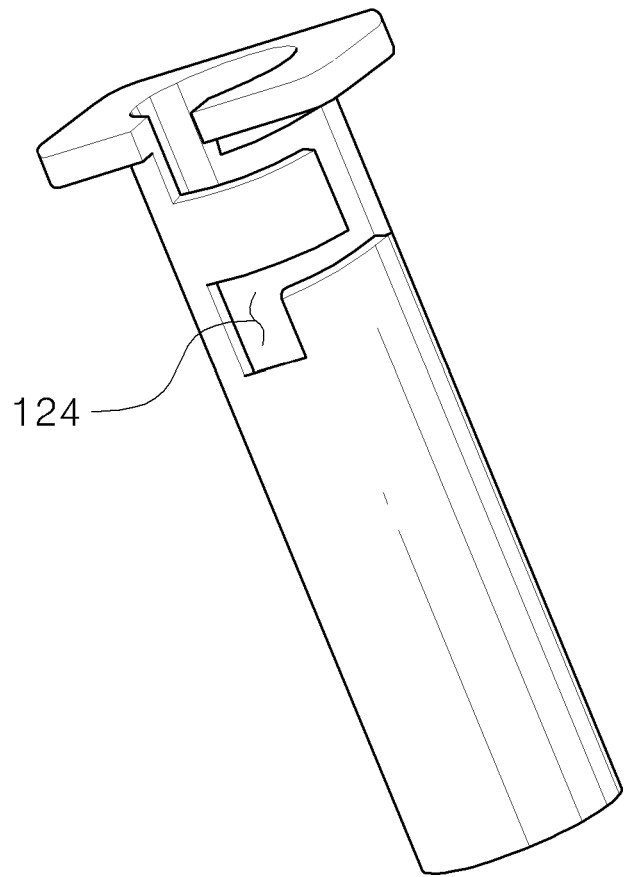
FIG. 3 is a perspective view of a tube of the sampler.
Figure 4:
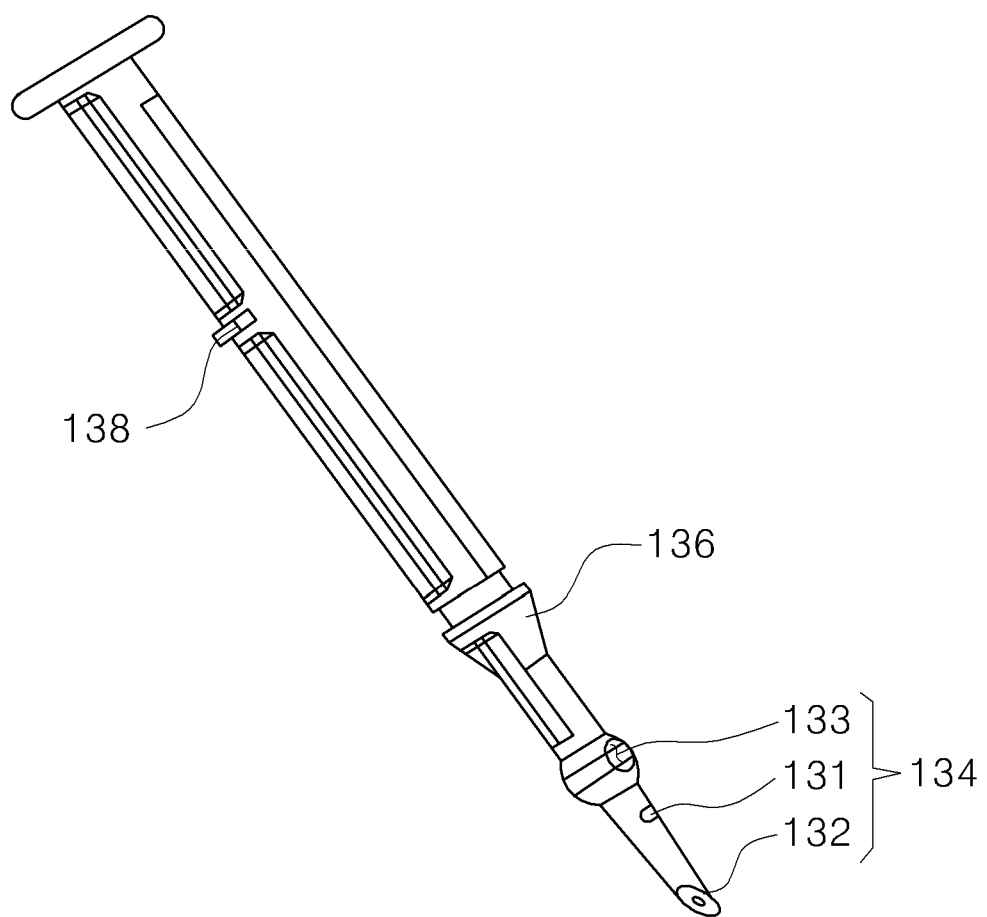
FIG. 4 is a perspective view of a movable bar of the sampler.

FIG. 1 is a sectional view showing an operational process of a sampler divided into three steps according to a first preferred embodiment of the present invention, FIG. 2 is a perspective view of a chamber of the sampler according to the first preferred embodiment, FIG. 3 is a perspective view of a tube of the sampler, and FIG. 4 is a perspective view of a movable bar of the sampler.

Referring to FIGS. 1 to 4, the sampler 100 according to the first preferred embodiment of the present invention includes: a chamber 110 accommodating a fluid or solid reagent therein and being sealed with penetrable films at both ends; a tube 120 joined with the chamber 110 at one side and having a hollow portion 122 therein; and a movable bar 130 having a tip 134, which has a specimen extracting portion 131 at one end, and being guided and moved through the hollow portion 122, whereby a specimen extracted by the specimen extracting portion 131 and the reagent are mixed when the tip 134 passes through one end of the chamber 110 and the reacted specimen is quantitatively discharged out when the tip 134 passes through the other end of the chamber 110.

The chamber 110 accommodates various reagents, such as dilution buffers or solid reagent materials, which can be mixed with the extracted specimen, according to use purposes so as to form a diluted solution or a mixed solution.

In other words, the sampler 100 according to the present invention is applicable in various fields, for instance, to dilute, to put and mix a fluid or solid reagent in the chamber 110, to fill biomolecules with affinity usable for chromatography to separate and refine, to put membranes to separate and refine, and so on.

Both ends of the chamber 110 are sealed with the penetrable films, wherein one end joined with the tube 120 is sealed by a pouch 116, so that the tip 134 perforates the pouch 116 so as to penetrate into the chamber 110 while the movable bar 130 moves.

Moreover, the chamber 110 includes an outlet 112 disposed at the middle portion of the other end for allowing the tip 134 to move forward, and the outlet 112 is also sealed with a penetrable discharge film 113. The chamber 110 and the discharge film 113 may be made of elastic materials, for instance, PE (Polyethylene) or other materials with elasticity, and may be manufactured by injection-molding using the elastic materials.

The discharge film 113 is formed thin, and hence, when a user pushes the movable bar 130, the tip 134 moves forward so as to penetrate the discharge film 113. In this instance, because the discharge film 113 is made of elastic material, when the tip 134 moves forward after penetrating the discharge film 113, the perforated edge portion of the discharge film 113 gets in contact with the periphery of the tip 134, and hence, the fluid does not leak through the perforated portion of the discharge film 113.

That is, because the discharge film 113 is made of the elastic material, it is rippedly perforated at a portion where an end of the tip 134 touches, and hence, there is no tolerance between the tip 134 and the perforated edge of the discharge film 113.

Here, the tip 134 is tapered, and the outlet 112 includes an inclined portion 114 having a shape corresponding to the shape of the tip 134 and getting in contact with the tip 134.

In this case, a range of the perforated discharge film 113 is wider as the tip 134 gradually moves forward, and when the discharge film 113 is perforated completely, the tip 134 moves no more.

In other words, when the discharge film 113 is perforated completely, because the outlet 112 having a predetermined diameter gets in contact with the tip 134 having a predetermined diameter and the tip 134 moves no more, a movement distance of the tip 134 can be regulated in such a manner that a size of the diameter is regulated, and a discharged amount can be regulated by the movement distance.

Furthermore, the tapered tip 134 gets in contact with the inclined portion 114 of the outlet 112 so as to keep a sealing state sufficiently strong to prevent that the fluid drops down between the tip 134 and the outlet 112.

In the meantime, the tip 134 includes: a discharge channel 132 for discharging the reacted specimen to the end of the tip 134; and a mixing hole 133 communicating with the specimen extracting portion 131 and the discharge channel 132 and having a space in which the specimen extracted by the specimen extracting portion 131 can be mixed with the reagent.

One end of the discharge channel 132 extends to the end of the tip 134 for discharging the reacted specimen, and the other end of the discharge channel 132 is communicated with the mixing hole 133. Additionally, the middle portion of the discharge channel 132 may be communicated with the specimen extracting portion 131 at right angles or at a predetermined angle. That is, the specimen extracting portion 131 and the mixing hole 133 are all communicated based on the discharge channel 132.

Now, relations in action among the specimen extracting portion 131, the discharge channel 132 and the mixing hole 133 will be described. The moment the specimen contained at a fingertip or in a blood tube touches the specimen extracting portion 131, due to the capillary phenomenon, it is sucked into a tube formed in the specimen extracting portion 131 so as to fill up the discharge channel 132.

In this instance, besides the specimen extracting portion 131, the discharge channel 132 can be used to extract the specimen using the capillary phenomenon in the same way.

Especially, a blood-gathering tube especially used in a hospital is formed long, and hence, is easy to extract the specimen through the discharge channel 132. Moreover, when the tip 134 is inserted into the chamber 110, because both ends of the discharge channel 132 are open, the reagent contained in the chamber 110 and the specimen positioned inside the discharge channel 132 are in contact with each other, and then, the specimen gets out the chamber 110.

When the specimen which fills the discharge channel 132 gets out the chamber 110, the reagent fills the inside of the discharge channel 132 from which the specimen goes out, and while the above process is repeated, the specimen and the reagent which fill the discharge channel 132 are mixed together so as to form a reacted specimen.

In this instance, the specimen which fills out the discharge channel 132 mainly gets out toward the mixing hole 133, and a reaction between the specimen and the reagent carried out inside the mixing hole 133 is spread into the chamber 110 on the basis of the mixing hole 133.

Meanwhile, the movable bar 130 may include a pressuring portion 136 which applies a predetermined pressure to the diluted solution inside the chamber 110 so as to quantitatively discharge the reacted specimen when the user presses the movable bar 130 more after the tip 134 penetrates the other end of the chamber 110, namely, the discharge film 113.

The pressuring portion 136 applies a predetermined pressure to the reacted specimen while entering the chamber 110, and then, pressurizes the reacted specimen till the tip 134 moves forward no more by getting in contact with the inclined portion 114 of the outlet 112 after the tapered tip 134 perforates the discharge film 113.

Additionally, during the above process, because the tip 134 advances to a predetermined distance, an equal value is always applied to the reacted specimen by the pressurizing portion 136, and hence, the reacted specimen of a fixed volume can be discharged. In this instance, when the user regulates the length of the tip 134 and the length of the guide hole 124 of the tube 120, a discharged volume of the fluid can be adjusted.

That is, the sampler 100 according to the present invention is constructed in such a manner that the tip 134 which extracted the specimen is inserted into the chamber 110 through one end of the chamber 110, in which the fluid is accommodated, so as to mix the specimen and the fluid to form a diluted solution, and then, the tip 134 is discharged and pressurized out through the other end of the chamber 110 so as to quantitatively discharge the reacted specimen.

In the meantime, the sampler 100 according to the present invention may further include: a guide protrusion 138 disposed at one side of the movable bar 130; and a guide hole disposed in the tube 120 for guiding a movement of the guide protrusion 138 and adjusting the movement of the movable bar 130 by steps.

As shown in FIGS. 1 and 3, the guide hole 124 is formed in three stages so as to divide the operational process of the sampler 100 into three steps.

Accordingly, in the state where the chamber 110 and the tube 120 are joined together, when the user manipulates the movable bar 130 in such a way that the guide protrusion 138 moves along the guide hole 124, the sampler 100 can easily carry out each of necessary steps of inserting the tip 134 into the chamber 110, diluting the specimen, and discharging the diluted solution.

In detail, the first step is to insert and fix the tip 134 into the chamber 110. In the first step, the tip 134 penetrates the pouch 116, which seals the upper face of the chamber 110, and goes toward the reagent contained in the chamber 110. Namely, the first step is to simply insert the tip 134 into the chamber 110.

Furthermore, when the user rotates and presses the movable bar 130 at 90 degrees, the second step is carried out. In the second step, the tip 134 advances till the end portion of the tip 134 perforates out the discharge film 113 of the outlet 112 of the chamber 110 a little. In this instance, because the chamber 110 is sealed by the pressurizing portion 136 located above the mixing hole 133 of the tip 134, the user shakes the sampler 100 so as to mix the specimen contained in the discharge channel 132 and the reagent contained in the chamber 110.

When the user rotates and presses the movable bar 130 in the opposite direction at 90 degrees, the third step is carried out. In the third step, the tip 134 completely penetrates through the discharge film 113 of the outlet 112 of the chamber 110, and in this instance, the diluted solution of the sealed state is discharged through an end of the discharge channel 132 of the tip 134 which advances while penetrating the discharge film 113.

In other words, in the sealed state, the inside fluid is discharged out by pressure applied into the chamber 110 by the pressurizing portion 136 as long as a distance that the tip 134 protrudes outwardly from the outlet 112. In this instance, the discharged volume of the fluid can be adjusted when the protruding distance of the tip 134 is regulated properly.

In the second step, because the discharge film 113 is torn minutely and the torn edge of the discharge film 113 surrounds the tip 134, there is no tolerance between the tip 134 and the discharge film 113.

Additionally, also in the third step, the perforated size of the discharge film 113 is gradually wider while the tip 134 advances outwardly, but because the chamber 110 and the discharge film 113 are made of the elastic material, the discharge film 113 is perforated according to the shape and the outer diameter of the tip 134, and hence, there is no tolerance between the tip 134 and the outlet 112.

In addition, in the state where the tip 134 advances in such a way that the discharge film 113 is perforated completely, because the inclined portion 114 fixes the tapered portion of the tip 134 so that the tip 134 advances no more, during this process, the tip 134 advances just to a predetermined distance so as to discharge a wanted volume.

Figure 5:
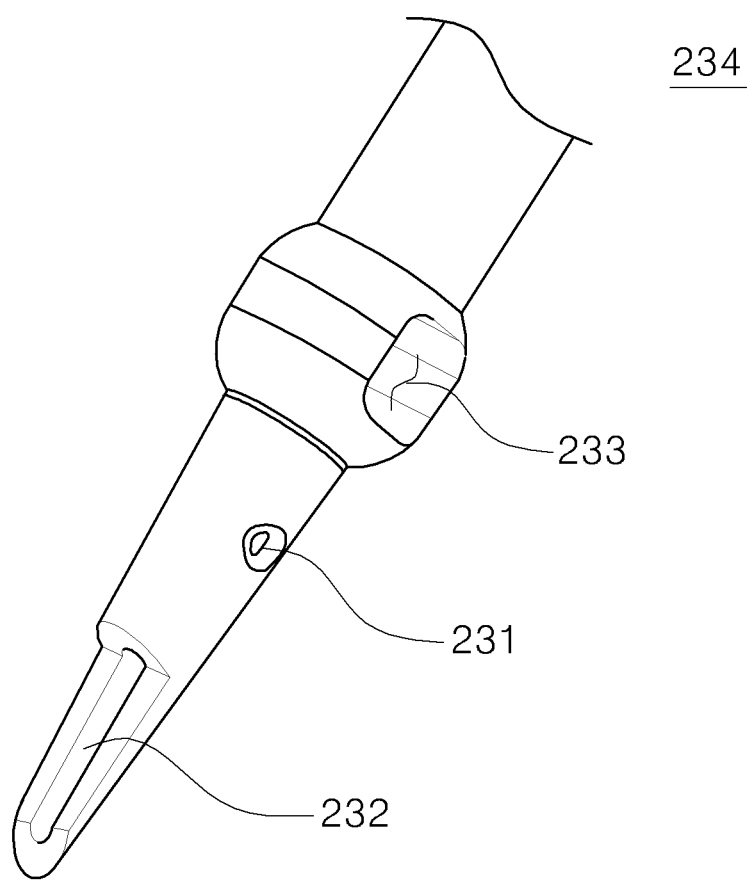
FIG. 5 is a partially perspective view of a tip of the sampler.
Figure 6:
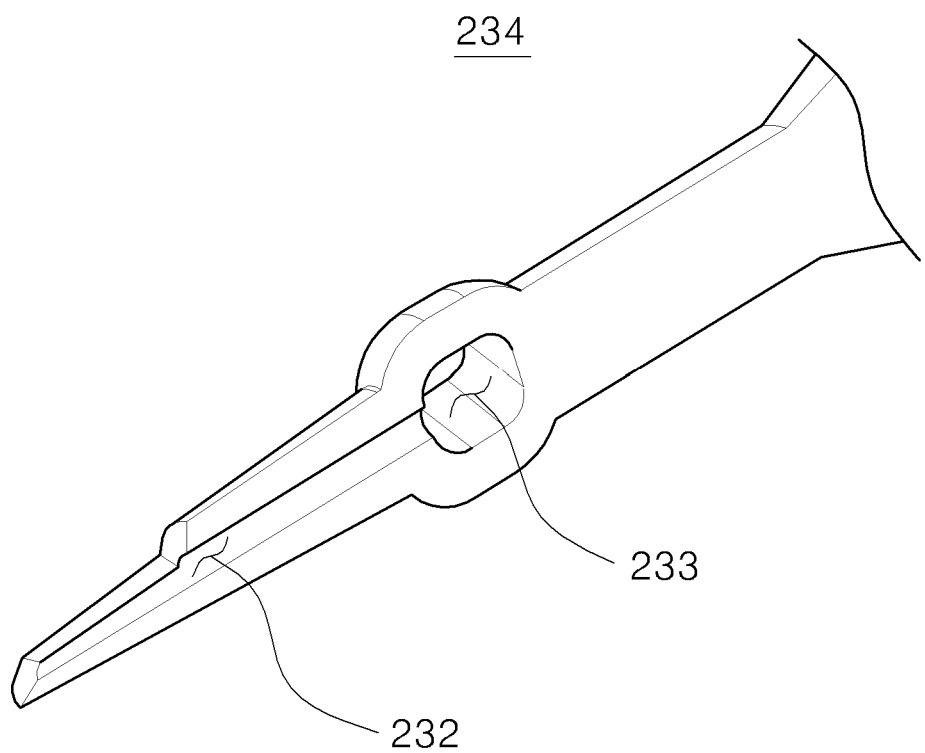
FIG. 6 is a partially perspective view showing the tip of FIG. 5 taken in longitudinal section.
Figure 7:
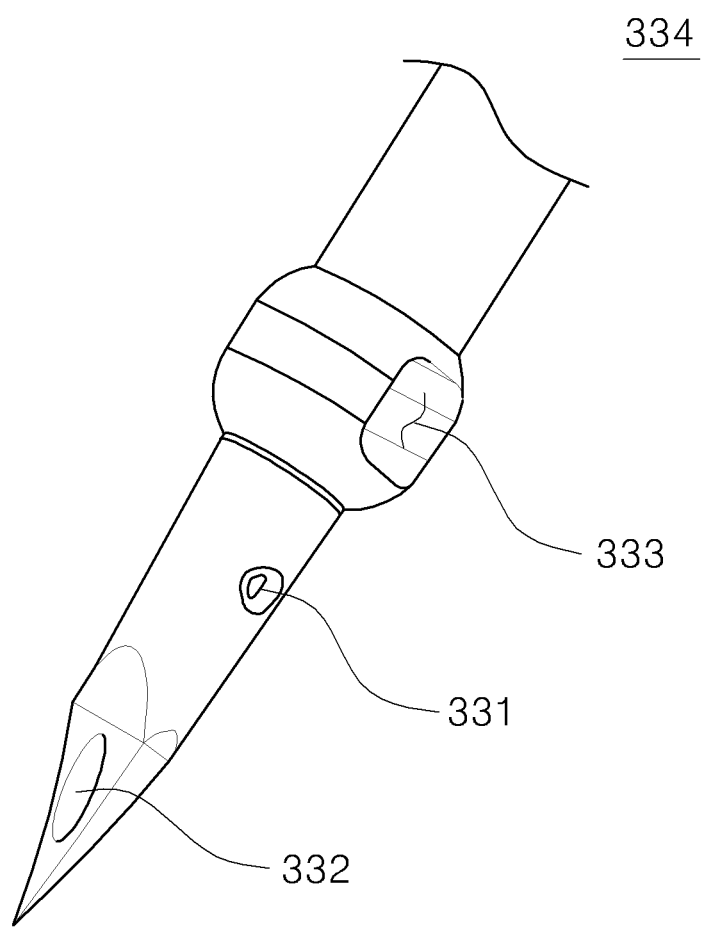
FIG. 7 is a partially perspective view of another example of the tip of the sampler.
Figure 8:
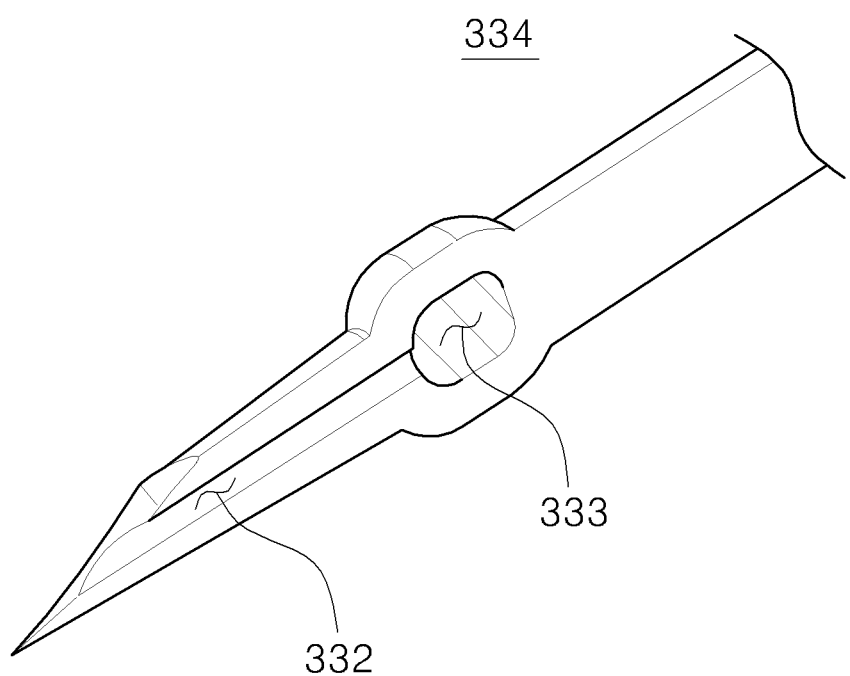
FIG. 8 is a partially perspective view showing the tip of FIG. 7 taken in longitudinal section.
Figure 9:
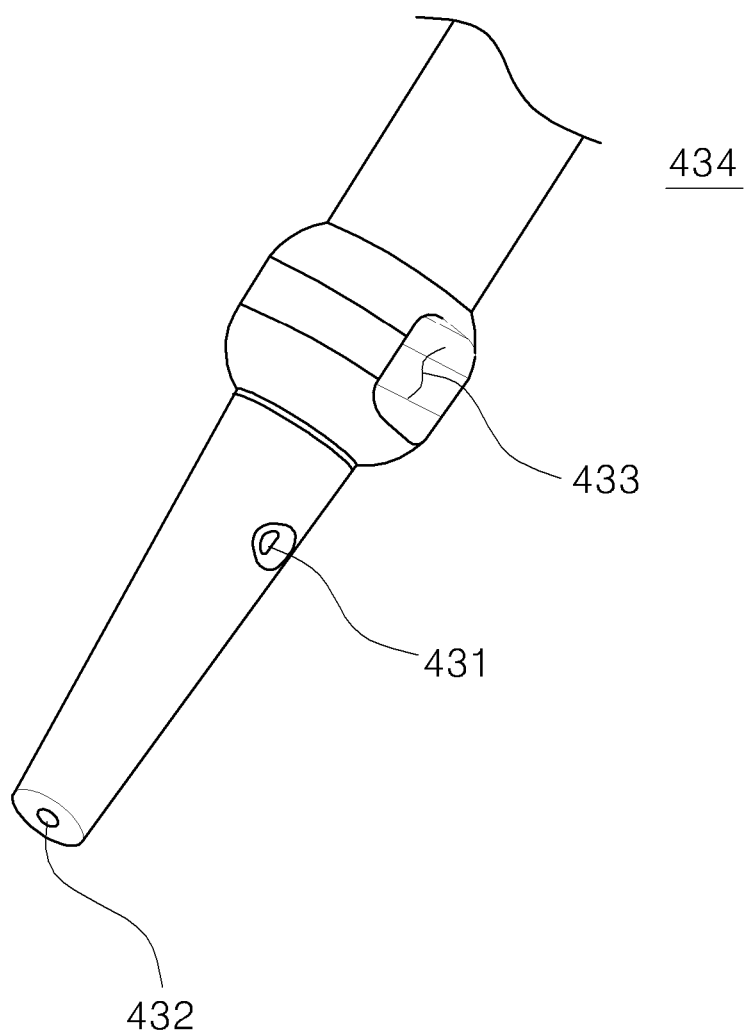
FIG. 9 is a partially perspective view of a further example of the tip of the sampler.
Figure 10:
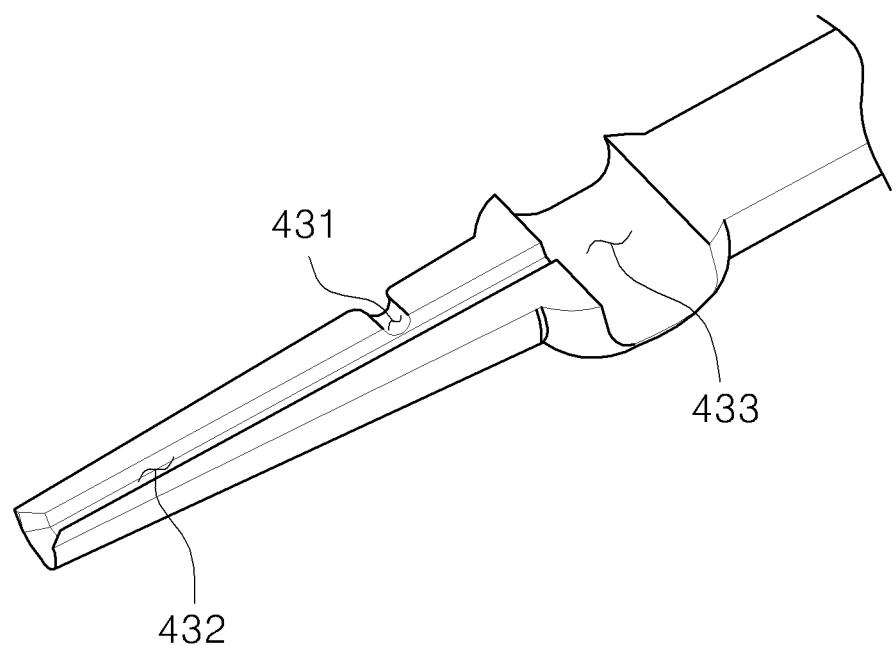
FIG. 10 is a partially perspective view showing the tip of FIG. 9 taken in longitudinal section.

FIG. 5 is a partially perspective view of the tip of the sampler, FIG. 6 is a partially perspective view showing the tip of FIG. 5 taken in longitudinal section, FIG. 7 is a partially perspective view of another example of the tip of the sampler, FIG. 8 is a partially perspective view showing the tip of FIG. 7 taken in longitudinal section, FIG. 9 is a partially perspective view of a further example of the tip of the sampler, and FIG. 10 is a partially perspective view showing the tip of FIG. 9 taken in longitudinal section.

Referring to FIGS. 5 to 10, tips 234, 334 and 434 of the sampler 100 according to the present invention have various shapes. The shapes of the tips 234, 334 and 434 may be varied according to materials of the chamber 110 and the discharge film 113, kinds of the reagent filling the inside of the chamber 110, and discharged volumes of the reacted specimen.

Of course, even though the shapes of the tips 234, 334 and 434 are changed, positions and connection relations of specimen extracting portions 231, 331 and 431, discharge channels 232, 332 and 432, and mixing holes 233, 333 and 433 are not changed.

Figure 11:
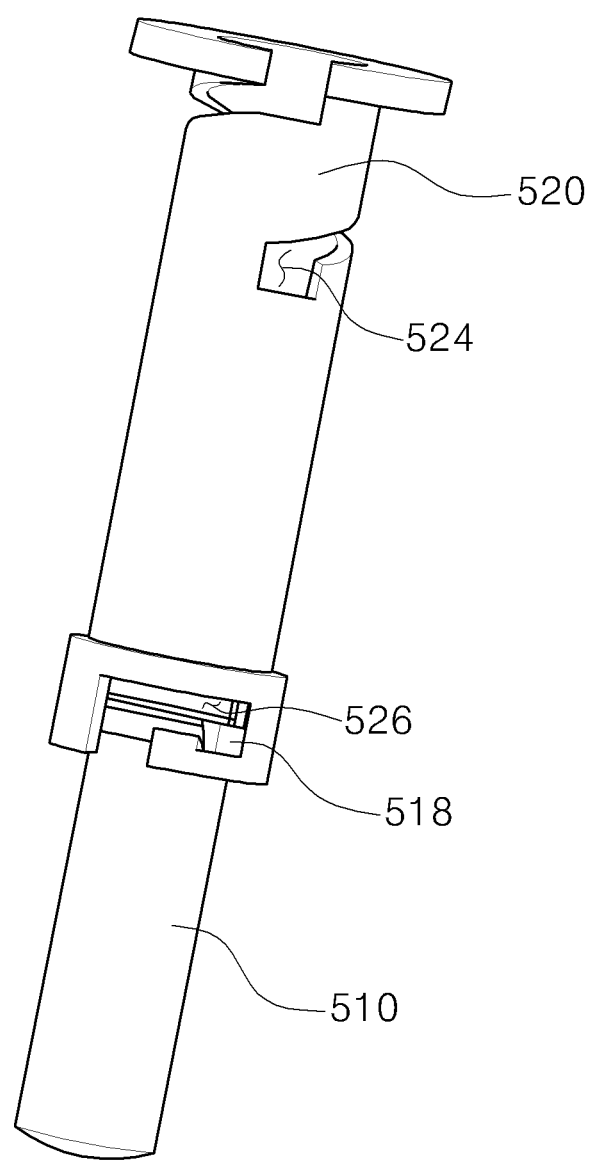
FIG. 11 is a perspective view showing joining relations among a guide hole, a tube and a chamber according to a second preferred embodiment of the present invention.
Figure 12:
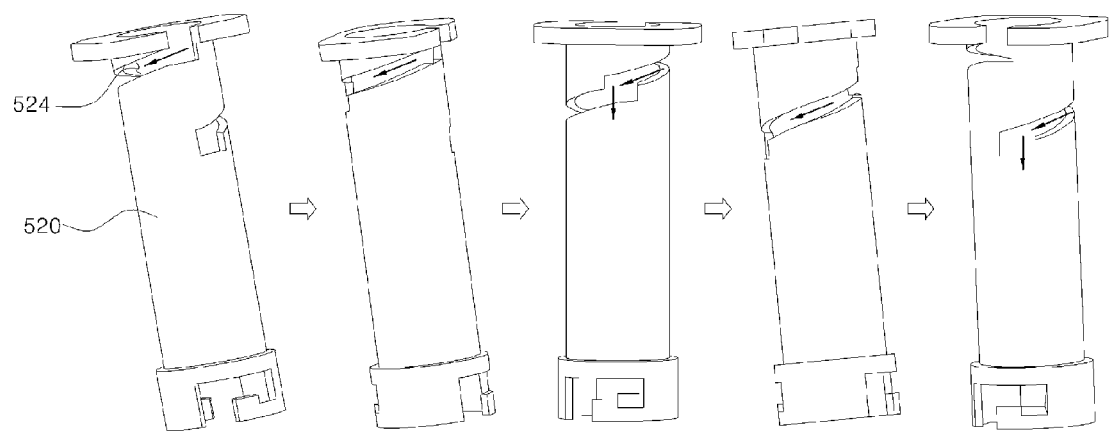
FIG. 12 is a flow chart showing an operational process of the sampler by the guide hole of FIG. 11.

FIG. 11 is a perspective view showing joining relations among a guide hole, a tube and a chamber according to a second preferred embodiment of the present invention, and FIG. 12 is a flow chart showing an operational process of the sampler by the guide hole of FIG. 11.

Referring to FIGS. 2, 11 and 12, the sampler 100 according to the present invention includes at least one annular protrusion 118 formed at one side of the chamber 110 in a circumferential direction so that the chamber 110 and the tube 120 can be fit and combined to each other.

Besides the above, the combination relation between the chamber 110 and the tube 120 can be achieved in various ways. The chamber 110 and the tube 120 may respectively have screw threads (not shown) so as to be screw-coupled with each other. As shown in FIG. 11, a chamber 510 may include a fitting protrusion 518 and a tube 520 may include a joining groove 526 formed corresponding to the fitting protrusion 518, so that the chamber 510 and the tube 520 can be combined with each other.

In the meantime, as shown in FIG. 12, as another example of the movable bar 130, a guide hole 524 is continuously formed in a slide type without any step. When the user slightly presses the movable bar, the movable bar 130 moves along the slide-type guide hole, so that insertion and discharge of the movable bar 130 are achieved at once.

Figure 13:
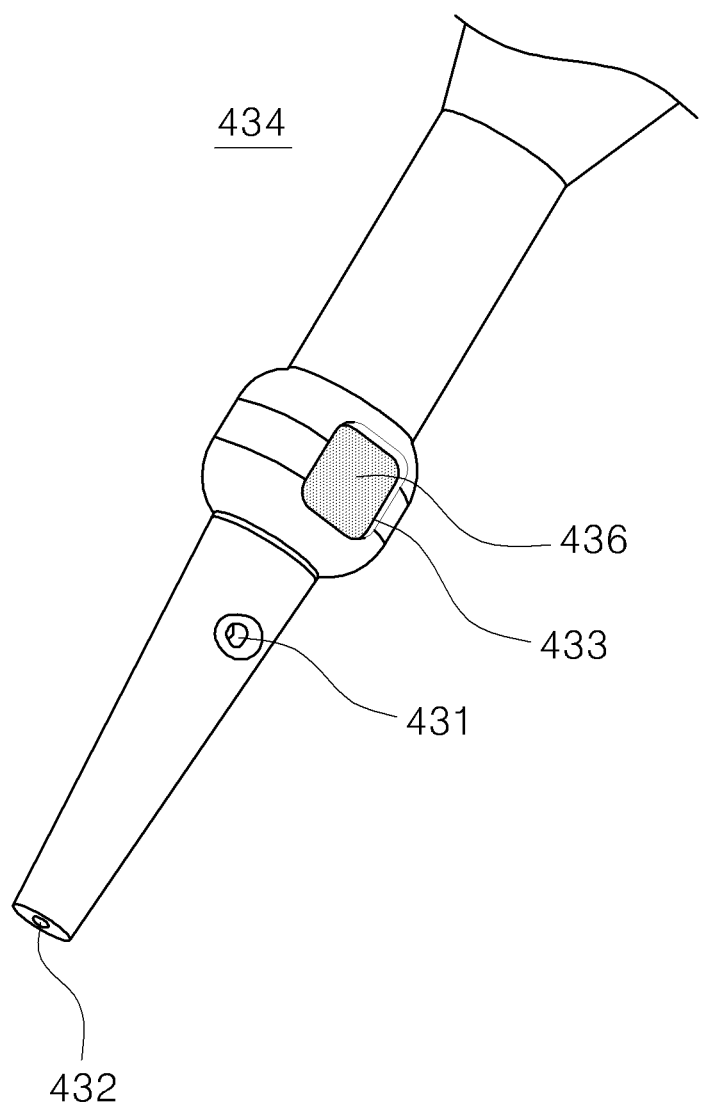
FIG. 13 is a partially perspective view showing a state where a tip mixing hole of FIG. 9 is filled with silica.
Figure 14:
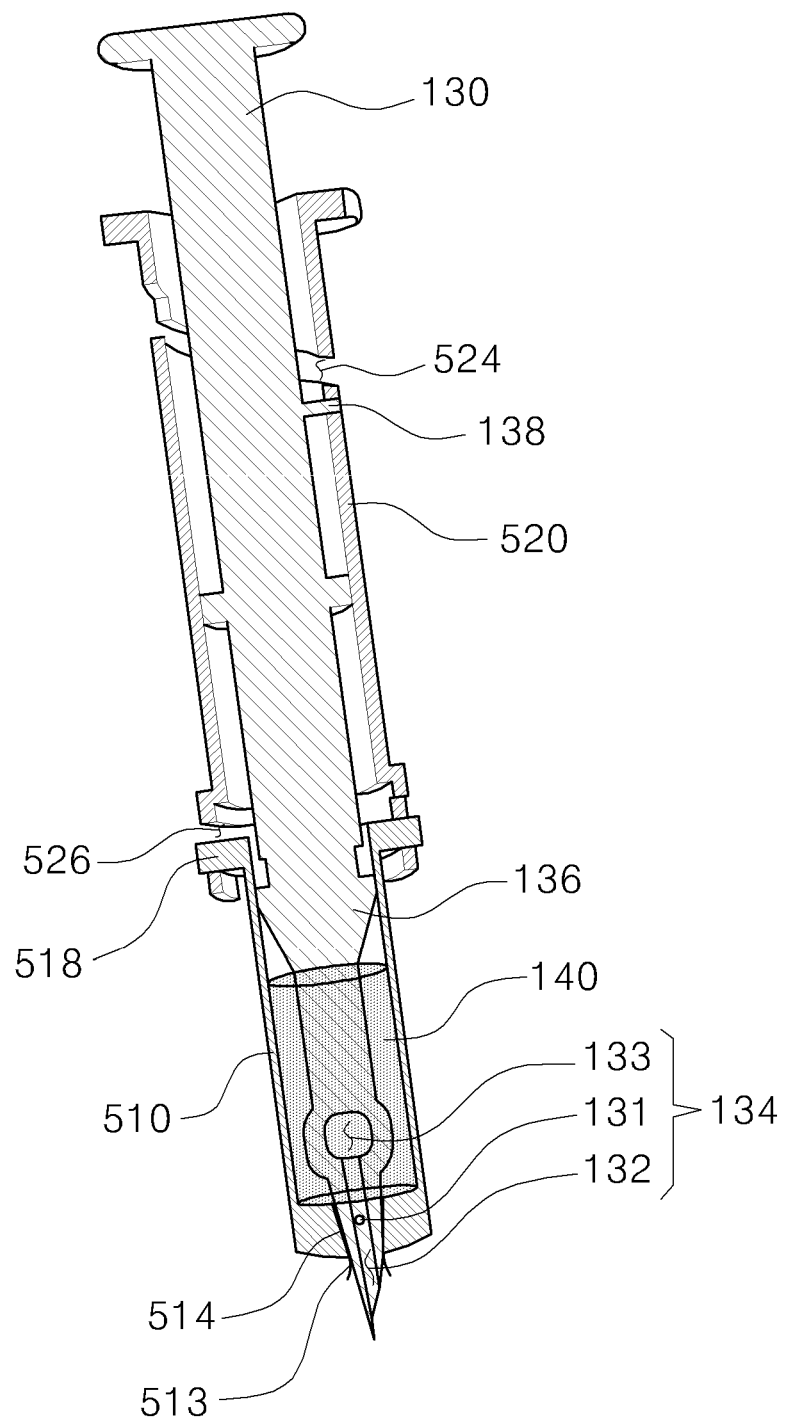
FIG. 14 is a sectional view showing a state where the sampler is filled with solid reagent, such as silica, and supporter.

FIG. 13 is a partially perspective view showing a state where a tip mixing hole of FIG. 9 is filled with silica, and FIG. 14 is a sectional view showing a state where the sampler is filled with solid reagent, such as silica, and supporter.

Referring to FIGS. 13 and 14, the reagent filling the chamber 510 includes at least one of silica particles which facilitate extraction of DNA or RNA by applying a physical force to a blood sample, antibodies selectively separating protein, and reagents utilized as supporters.

Moreover, the sampler 100 according to the present invention may further include reactants for supporting the silica particles or biomolecular particles filling the inside of the chamber 510 in order to facilitate extraction of DNA or RNA by applying the physical force to the blood sample when the pressurizing portion 136 applies pressure.

As an example of using silica, through preprocessing using silica, a multiple response sampling is possible. As shown in FIG. 13, a sample-treated silica 436 is inserted into the mixing hole 433, and at the time of extraction of a specimen, the reagent and the specimen treated to the silica sample 436 are reacted, and then, the tip 434 is inserted into the chamber 510 so that the specimen previously reacted with the reagent is reacted with the dilution buffer, thereby, the sampler according to the present invention can reduce the two or three steps to one step of the process.

Furthermore, after the above process, if another reaction and treatment is needed, the chamber 510 filled with another dilution buffer or fluid 140, which is a preprocessed sample, may be applied so as to continuously carry out additional reaction. Additionally, the chamber 510 can be changed utilizing the additional reaction in such a way as to be applicable to various specimen samplings, such as extraction of DNA or RNA and others.

Figure 15:
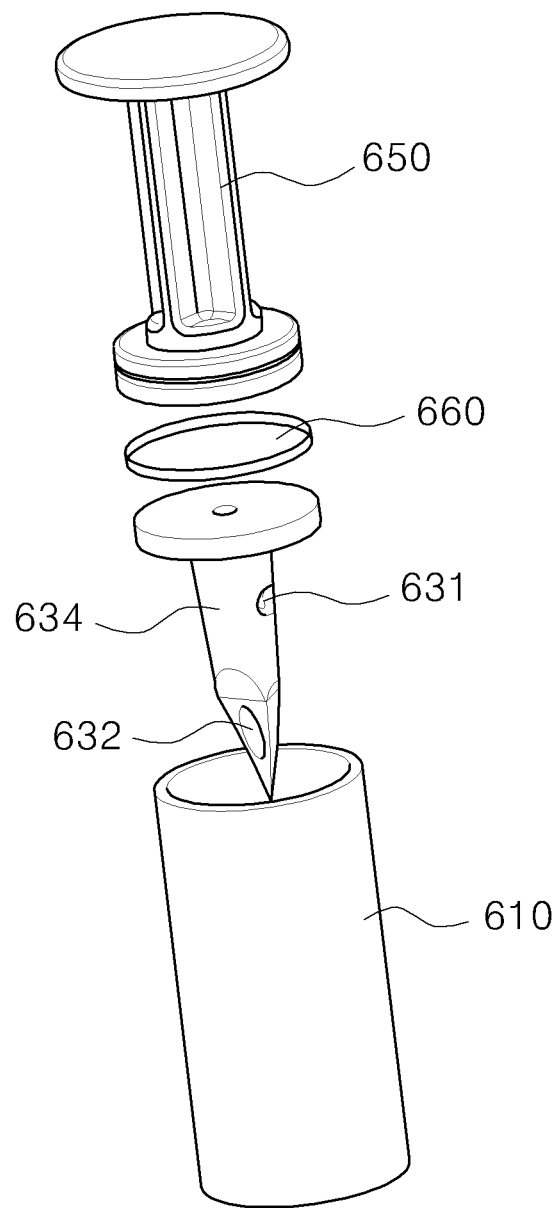
FIG. 15 is an exploded perspective view showing a structure of a sampler according to a third preferred embodiment of the present invention.
Figure 16:
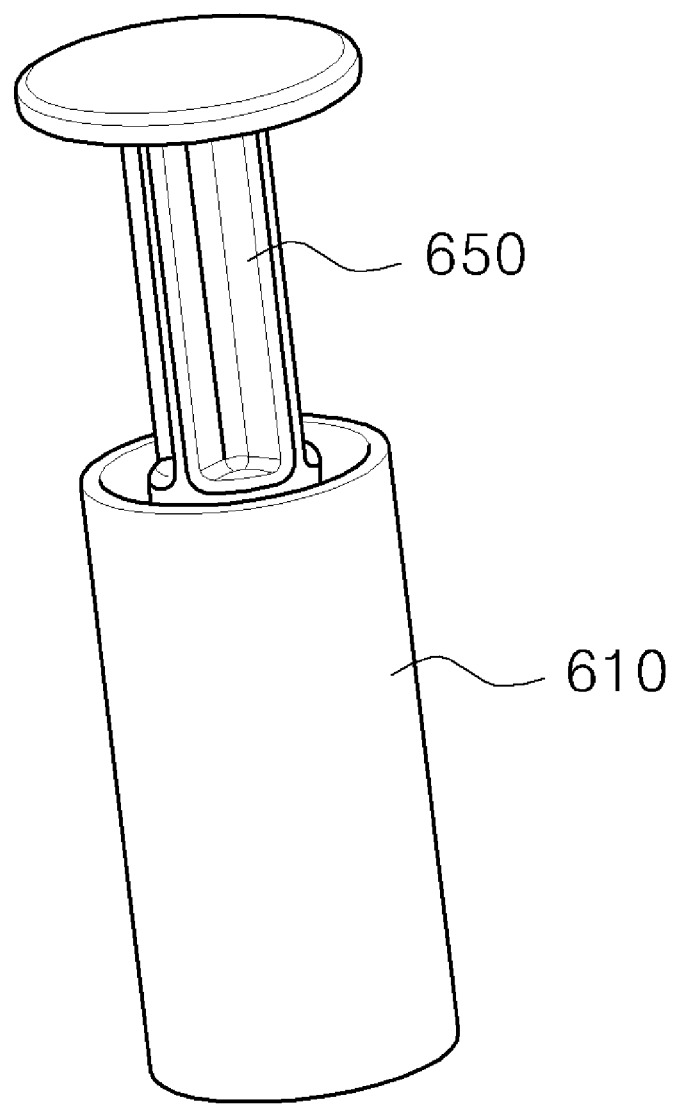
FIG. 16 is a perspective view showing an assembled state of the sampler of FIG. 15.
Figure 17:
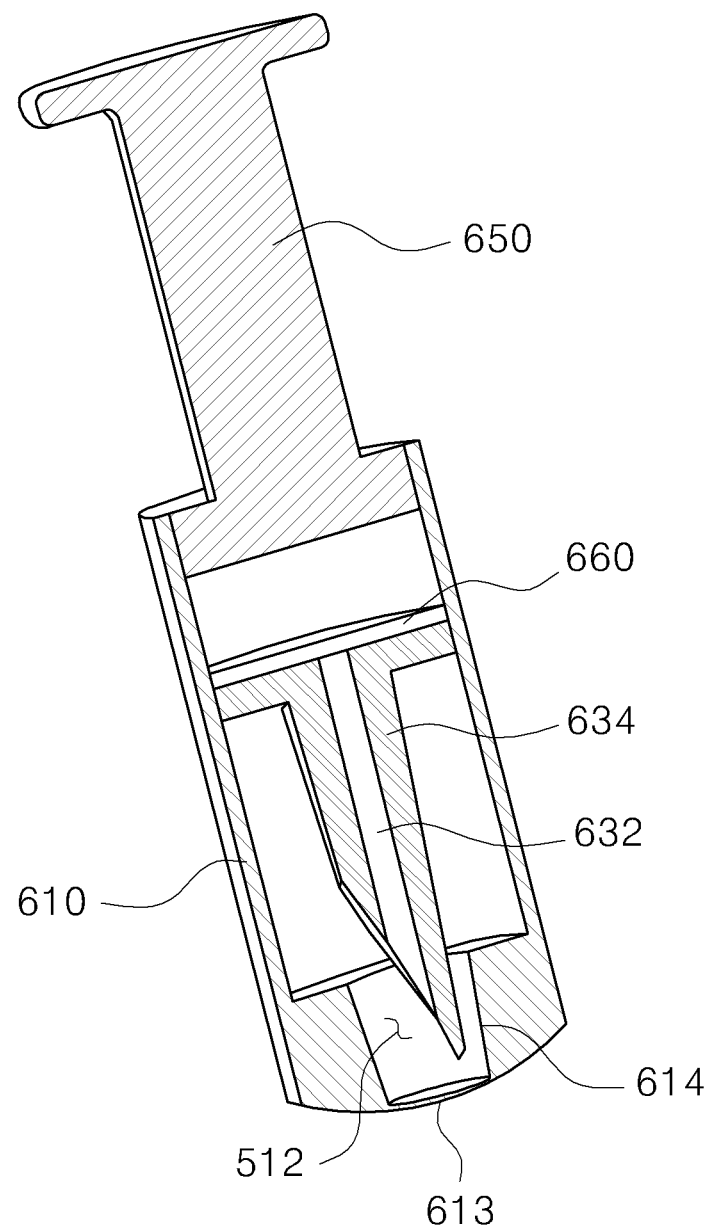
FIG. 17 is a sectional view of the sampler of FIG. 16.

FIG. 15 is an exploded perspective view showing a structure of a sampler according to a third preferred embodiment of the present invention, FIG. 16 is a perspective view showing an assembled state of the sampler of FIG. 15, and FIG. 17 is a sectional view of the sampler of FIG. 16.

Referring to FIGS. 15 to 17, the sampler according to the third preferred embodiment of the present invention includes: a chamber 610 having a space for accommodating a fluid or solid reagent therein; a tip 634 disposed inside the chamber 610 and having a discharge channel 632 for discharging a specimen which is mixed with the reagent so as to be reacted; and a cylinder 650 for moving the tip 634, wherein the tip 634 perforates the other end of the chamber 610 so as to quantitatively discharge out the reacted specimen. Moreover, the sampler according to the present invention may further include a membrane 660 for refining and discharging the reacted specimen.

In this embodiment, the tip 634 may be provided in a state where it is inserted into the chamber 610. The reagent is put in a space between the tip 634 and the cylinder 650 so as to cause a reaction, and after that, when the user presses the cylinder 650, the reacted specimen is discharged through the discharge channel 632. The action relationship of the tip 634, an outlet 612, a discharge film 613, an inclined portion 614 and other parts in relation with the mechanism to discharge the reacted specimen are the same as the above embodiments of the present invention, and hence, its detailed description will be omitted.

As described above, the specimen is extracted through a specimen extracting portion 631 and is mixed with the reagent, but it is also possible that the specimen is extracted by another extracting tool and inserted into a space between the tip 634 and the cylinder 650 together with the reagent so as to be reacted.

As shown in FIG. 17, the membrane 660 is attached to an end of the tip 634 in order to carry out separation and refinement when the reacted specimen accommodated in the space between the tip 634 and the cylinder 650 is discharged.

Now, examples of using the sampler according to this embodiment will be described as follows.

First, the tip 634, the membrane 660 and the reagent such as a buffer are provided inside the chamber 610 in a sealed state. In this case, after the user opens the sealed pouch, the user puts the specimen into the chamber 610 so as to quantitatively discharge the reacted specimen using the cylinder 650 without applying additional reagent.

Of course, a buffer with different property may be added and preprocessed to carry out other work.

Second, only the tip 634 and the membrane 660 may be provided inside the chamber in a sealed state. In this case, after the user opens the sealed pouch, the user can use the specimen together with a wanted buffer. In this instance, the specimen can be extracted using the specimen extracting portion 631 disposed in the tip 634, and a specimen extracted by another extracting tool may be added together with a buffer.

In the above two cases, different chamber sets 610 having buffers of different purposes may be used for different purposes through various processes.

Moreover, the preprocessed membrane 660 may cause a chemical or biotic response, such as antigen reaction and antibody reaction by absorbing a sample. Alternatively, after a sample such as whole blood is put on the membrane 660 with tiny pores, the sample is mashed by the cylinder 650 so as to cause cell lysis of red blood cells (RBCs).

Figure 18:
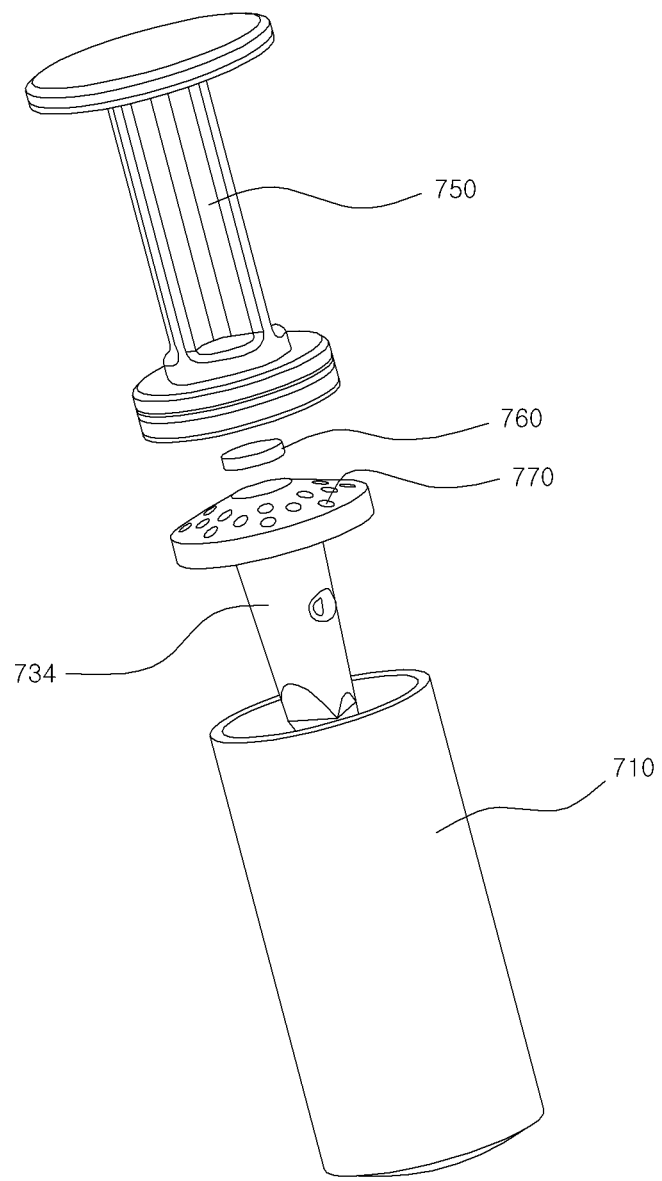
FIG. 18 is an exploded perspective view showing a structure of a sampler according to a fourth preferred embodiment of the present invention.
Figure 19:
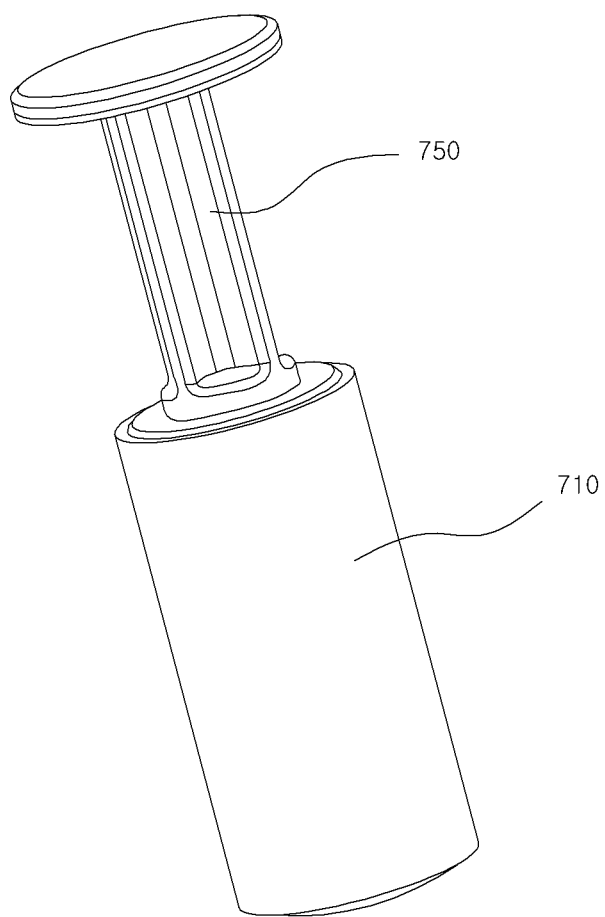
FIG. 19 is a perspective view showing an assembled state of the sampler of FIG. 18.
Figure 20:
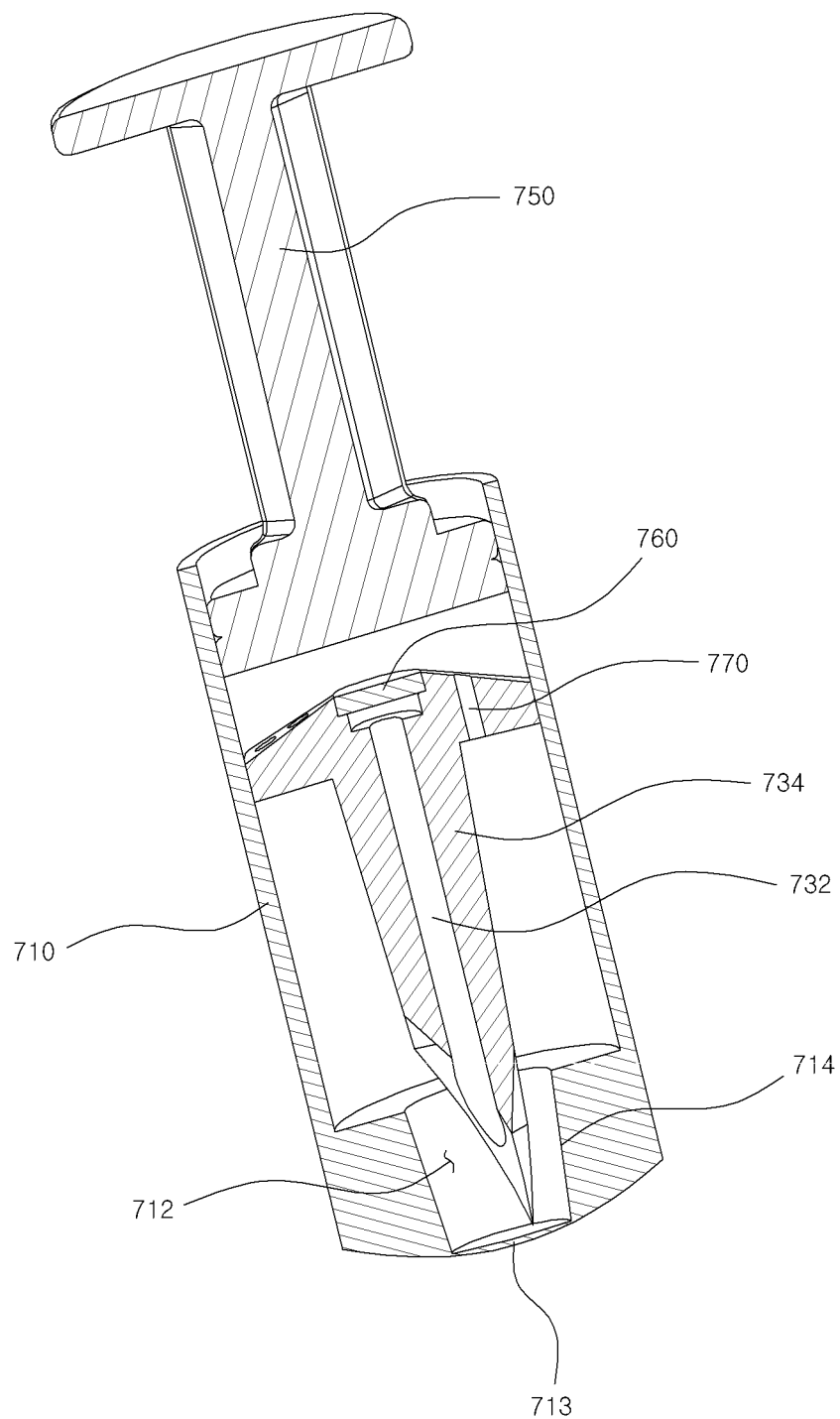
FIG. 20 is a sectional view of the sampler of FIG. 18.

FIG. 18 is an exploded perspective view showing a structure of a sampler according to a fourth preferred embodiment of the present invention, FIG. 19 is a perspective view showing an assembled state of the sampler of FIG. 18, and FIG. 20 is a sectional view of the sampler of FIG. 18.

Referring to FIGS. 18 to 20, a tip 734 of the sampler according to the fourth preferred embodiment of the present invention includes at least one separation hole 770 for separating a wanted material when centrifugation is carried out after a chamber 710 is mounted in a centrifuge.

Also in this embodiment, the tip 734 may be provided in a state where it is inserted into the chamber 710. A reagent is put in a space between the tip 734 and the cylinder 750 so as to cause a reaction, and then, the user presses the cylinder 750 so that the reacted specimen can be discharged through a discharge channel 732. The action relationship of the tip 734, an outlet 712, a discharge film 713, an inclined portion 714 and other parts in relation with the mechanism to discharge the reacted specimen are the same as the above embodiments of the present invention, and hence, its detailed description will be omitted.

Here, a membrane 760 may be interposed at the middle portion of one end of the tip 734 where the discharge channel 732 starts. Moreover, a plurality of separation holes 770 may be formed on the basis of the membrane 760 in such a way as to penetrate the end of the tip 734.

Now, an applicable example of the sampler will be described as follows.

After whole blood is put into the space between the cylinder 750 and the tip 734 and the chamber 710 is mounted in the centrifuge, when centrifugation is carried out, centrifugation is carried out in a state where red blood cells (RBCs) and white blood cells (WBCs) which are relatively larger remain on the tip 734 because they do not pass through the separation holes 770. Furthermore, in the above state, cell lysis of the red blood cells and the white blood cells may occur or the red blood cells and the white blood cells are additionally reacted with other reagents so as to be preprocessed.

Additionally, the sampler according to this embodiment may be applied to separate constituents of various reaction samples, and after the reaction, the sampler may be also applied to concentrate the reacted sample after the chamber 710 is mounted in the centrifuge. In this instance, the size of the separation holes 770 may be varied according to sizes and specific gravities of materials to be separated.

In order to check the quantitative discharge performance of the sampler according to the preferred embodiments of the present invention, the following test has been carried out.

Used device: Dilution sampler
Standard sample: Dark Red 1 um Bead (660/680)
Dilution buffer: PBS buffer
Measuring device: TECAN
How to test
1. Obtain a standard sample using the tip of the sampler. (about 7 ul)
2. Prepare the chamber filled with the dilution buffer of a predetermined multiple in the volume of the tip.
3. Insert the tip in which the standard sample is attached into the chamber.
4. Shake the assembly of the tip and the chamber several times so as to mix the standard specimen and the dilution buffer.
<Check the Mixed State of the Standard Sample and the Dilution Buffer in the Sampler/Check Dilution CV Between Samplers>

5. Push the tip in the direction of the outlet of the chamber so as to perforate the outlet and drop the mixed buffer on a 96 wall plate.

6. Measure fluorescence using TECAN

<Measurement of Discharge Amount According to a Dilution Ratio of Mixed Buffer>

5-1. Push the tip in the direction of the outlet so as to penetrate the outlet and drop the mixed buffer on a plate which has been previously weighed.

6-1. Check weight of the plate.

Test result

<Check the Mixed State of the Standard Sample and the Dilution Buffer in the Sampler/Dilution Between Samplers>

Fluorescence Intensity

|  | #1 | #2 | #3 | #4 | #5 | Avg. | STDEV | CV |
|---|---|---|---|---|---|---|---|---|
| 1/50 dilution | 56085 | 54651 | 55405 | 55904 | 53969 | 55202.8 | 885.662 | 1.60438 |
| 1/100 dilution | 35993 | 34627 | 35183 | 35227 | 36162 | 35438.4 | 632.35 | 1.78436 |

It was confirmed that the samples in the samplers were diluted in a similar level when the samples were diluted at the same rate, and hence, it ensured stability in dilution at a fixed rate.

<Measurement of Discharge Amount According to a Dilution Rate of the Mixed Buffer>

Discharged Weight (Ug)

|  | 1/50 dilution | 1/100 dilution |
|---|---|---|
| 1 | 201.7 | 563.4 |
| 2 | 191.9 | 561.4 |
| 3 | 190.5 | 561.3 |
| 4 | 193.9 | 560.3 |
| 5 | 214.8 | 564.7 |
| Avg | 198.56 | 562.22 |
| STDEV | 10.06 | 1.79 |
| CV | 5.07 | 0.32 |

It was confirmed that volumes of buffers discharged from the samplers were on a similar level when the samples were diluted at the same rate and discharged amounts of the samplers were different according to volumes of the dilution buffers differently filling the chambers according to dilution rates. Additionally, the discharged amounts can be controlled according to the volumes of the dilution buffers.

Figure 21:
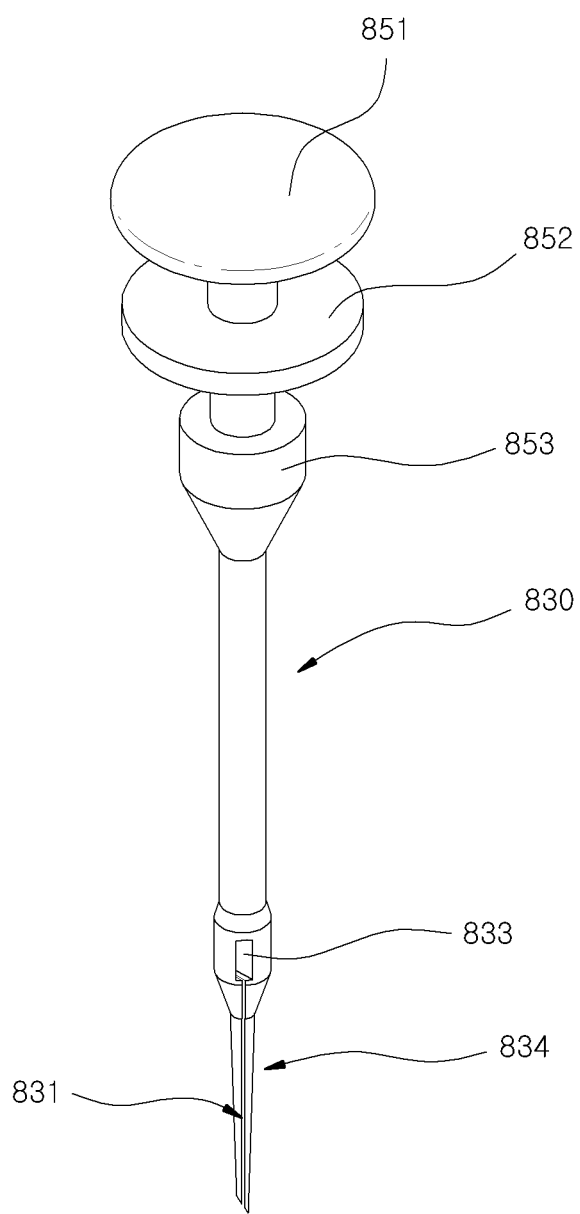
FIG. 21 is a perspective view of a movable bar of a sampler according to a fifth preferred embodiment of the present invention.
Figure 22:
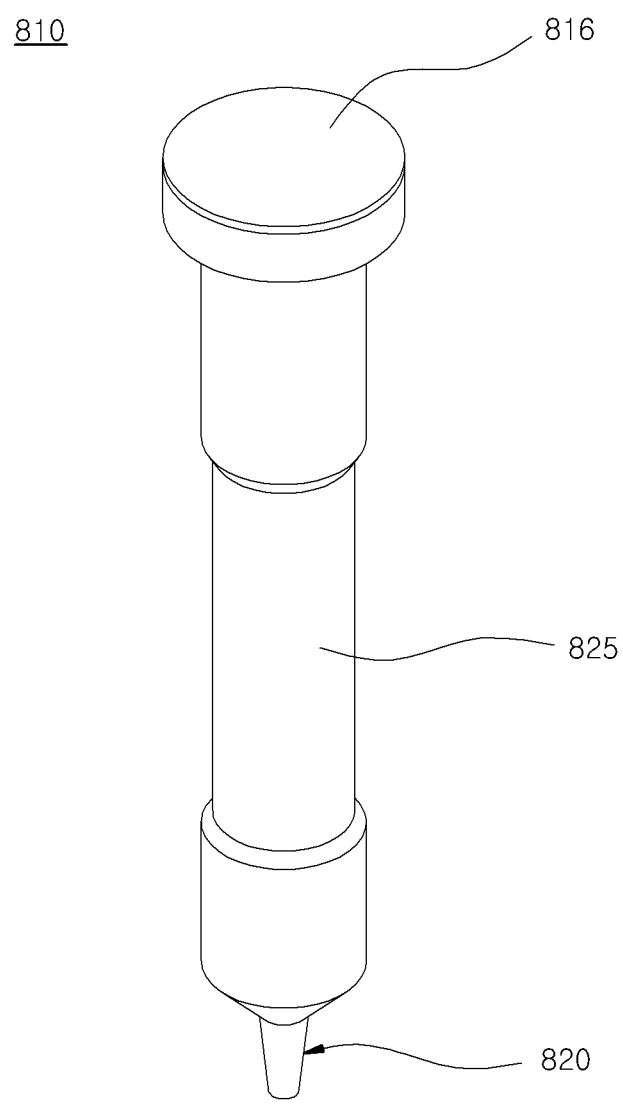
FIG. 22 is a perspective view of a chamber of the sampler according to the fifth preferred embodiment.
Figure 23:
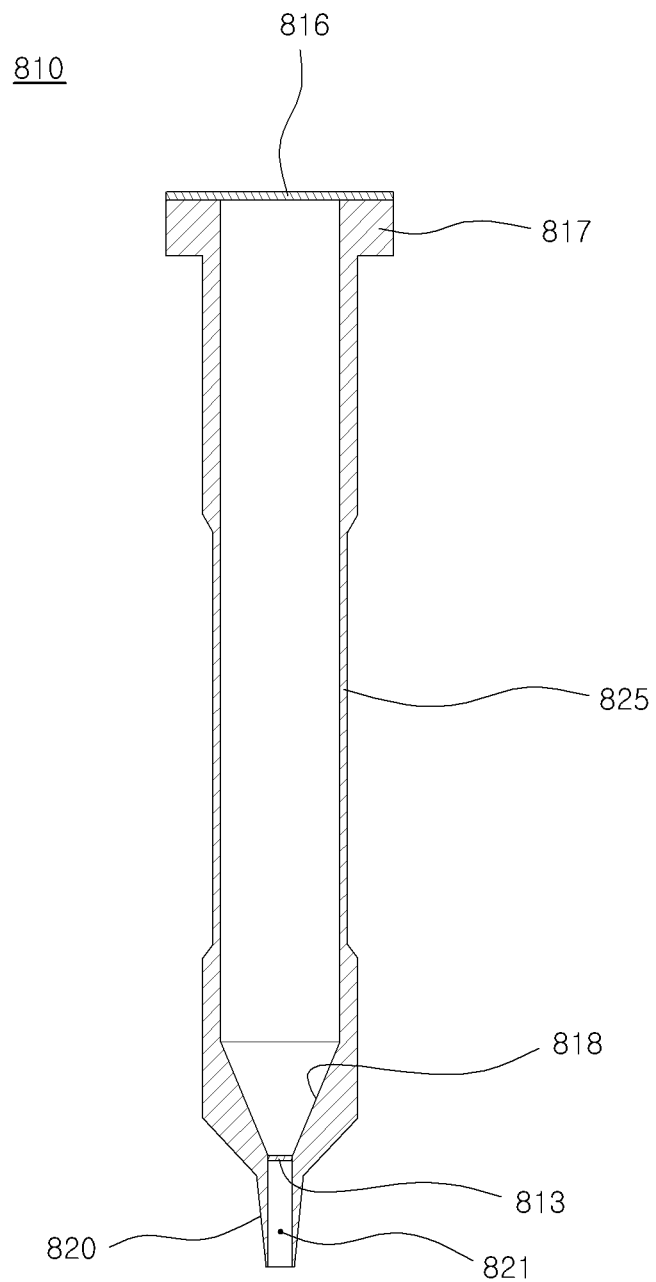
FIG. 23 is a sectional view of the chamber of the sampler according to the fifth preferred embodiment.

FIG. 21 is a perspective view of a movable bar of a sampler according to a fifth preferred embodiment of the present invention, FIG. 22 is a perspective view of a chamber of the sampler according to the fifth preferred embodiment, and FIG. 23 is a sectional view of the chamber of the sampler according to the fifth preferred embodiment.

As shown in FIGS. 21 to 23, the sampler according to the fifth preferred embodiment of the present invention includes a chamber 810 and a tip 834. Here, the tip 834 has a specimen extracting portion 831 formed at one end portion to accommodate an extracted specimen. Moreover, the chamber 810 has penetrable films formed at both ends thereof and accommodates a reagent contained therein. In a state where the tip 834 penetrates into the chamber 810 till shooting out through the chamber 810, when a pressing portion 825 of the chamber 810 is pressed, the reacted specimen is drippily discharged in a fixed quantity.

In detail, the chamber 810 includes a penetrable pouch 816 disposed at one end portion, and a penetrable discharge film 813 disposed at the other end portion.

Therefore, the chamber 810 are respectively sealed at both sides by the pouch 816 and the discharge film 813 and includes a sealed space therein. In the sealed space, a fluid or solid reagent is accommodated in safety without leakage.

Here, the reagent may be provided in a state where it fills the space in order to dilute a specific specimen at a certain ratio.

Moreover, it is preferable that the chamber 810 further includes a flange portion 817 formed at one end portion thereof.

The flange portion 817 serves to prevent deformation, such as bending, of the chamber 810 by increasing intensity of the other end portion of the chamber 810 and to effectively stop a stopper 852 which will be described later.

Furthermore, the chamber 810 may further include a discharge part 820 disposed at the other end portion.

Here, it is preferable that the discharge part 820 extends in a longitudinal direction of the chamber 810.

Additionally, it is preferable that the discharge part 820 has a discharge passage 821 formed therein, and the discharge passage 821 is separated from the inside space of the chamber 810 by the discharge film 813.

That is, when the discharge film 813 is torn or perforated, the inside space of the chamber 810 and the discharge passage 821 are connected with each other.

Moreover, it is preferable that the discharge part 820 is detachably joined to the other end portion of the chamber 810.

For this, the discharge part 820 can be detachably joined to the chamber 810 through one of various joining methods, such as a forcedly fitting method, a clamping method or a screw coupling method, and is not restricted to a specific method.

In the meantime, the tip 834 has a specimen extracting portion 831 for accommodating the extracted specimen. Here, it is preferable that the specimen extracting portion 831 is formed in a longitudinal direction of the tip 834 and both sides of the specimen extracting portion 831 are opened toward the outside of the tip 834.

Furthermore, it is preferable that the specimen extracting portion 831 is formed in such a manner that one end portion of the specimen extracting portion 831 is opened outwardly through one end portion of the tip 834.

Additionally, preferably, the specimen extracting portion 831 extends toward the other end portion of the tip 834 and has a mixing hole 833 formed at the end portion.

It is also preferable that both sides of the mixing hole 833 are opened toward the outside of the tip 834, and is filled with the specimen extracted by the specimen extracting portion 831. Therefore, the volume of the specimen which will be accommodated in the mixing hole 833 can be regulated according to the size of the mixing hole 833, and hence, a received dose of the specimen can be kept constantly.

In this instance, because the specimen is accommodated in the specimen extracting portion 831 and the mixing hole 833, it is natural that the total received dose of the specimen can be kept constantly by regulating the size of the specimen extracting portion 831 together with the size of the mixing hole 833.

Additionally, it is preferable that a movable bar 830 is formed at the other end portion of the tip 834 in the longitudinal direction of the tip 834, and preferably, the movable bar 830 is formed integrally with the tip 834.

In addition, the movable bar 830 includes a pressing plate 851, a stopper 852, and a pressurizing portion 853.

Preferably, the pressing plate 851 is formed at an end portion of the movable bar 830, and the stopper 852 and the pressurizing portion 853 are formed in order in the direction of the tip 834.

Here, it is preferable that the pressurizing portion 853 is formed in such a manner that the outer diameter of the pressurizing portion 853 corresponds to the inner diameter of the tube 870. Through the above, the outer face of the pressurizing portion 853 gets in contact with the inner face of the tube 870.

Moreover, the stopper 852 is disposed between the pressing plate 851 and the pressurizing portion 853, and has an outer diameter larger than an inner diameter of the tube 870.

That is, it is preferable that the stopper 852 has a diameter as larger as one side of the stopper 852 gets in contact with one side of the flange portion 817.

Figure 24:
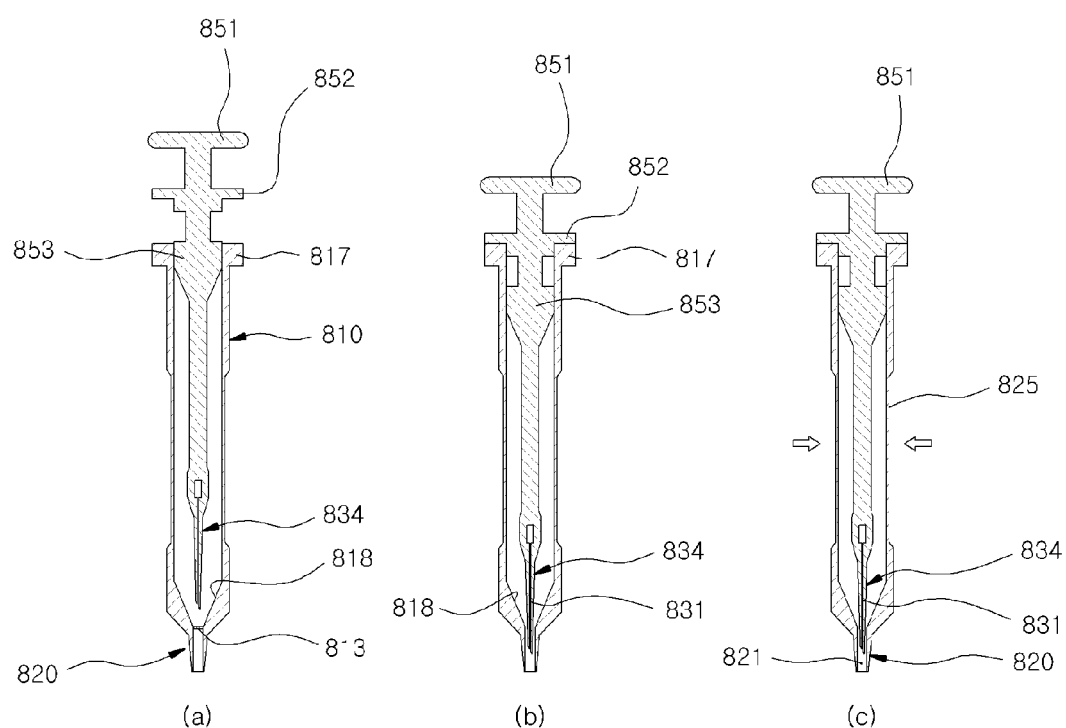
FIG. 24 is a sectional view showing an operational state of the chamber and the movable bar of the sampler according to the fifth preferred embodiment.
Figure 25:
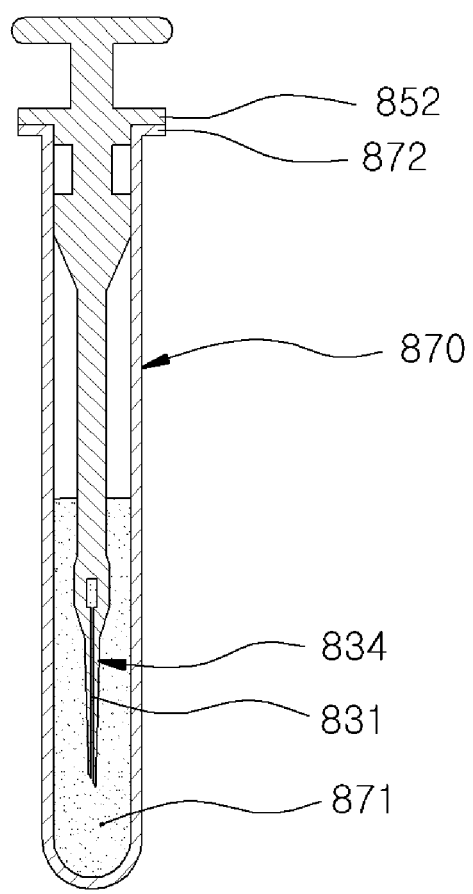
FIG. 25 is a sectional view showing a method of extracting a specimen using a tip of the sampler according to the fifth preferred embodiment.

FIG. 24 is a sectional view showing an operational state of the chamber and the movable bar of the sampler according to the fifth preferred embodiment, and FIG. 25 is a sectional view showing a method of extracting a specimen using a tip of the sampler according to the fifth preferred embodiment.

First, as shown in FIG. 24(*a*), when the tip 834 penetrates through the pouch 816 and is inserted into a portion of the chamber 810 (preferably, the tip 834 does not reach the discharge film 813), the pressurizing portion 853 is located inside the other end portion of the chamber 810.

Here, the outer face of the pressurizing portion 853 gets in contact with the inner face of the chamber 810, and hence, the fluid or solid reagent can be accommodated in the chamber 810 in safety.

Additionally, the specimen accommodated in the specimen extracting portion 831 and the reagent are mixed together, so that the reacted specimen is formed.

In this instance, because both sides and one end portion of the specimen extracting portion 831 are opened, the specimen and the reagent can be effectively mixed together inside the chamber 810.

After that, as shown in FIG. 24(*b*), when an external force is applied to the pressing plate 851, the movable bar 830 is moved, and hence, the tip 834 penetrates through the discharge film 813.

Moreover, the tip 834 penetrates the discharge film 813 and protrudes outwardly is located inside the discharge passage 821.

In this instance, the stopper 852 stops when it gets in contact with the flange portion 817, and hence, the movable bar 830 also stops.

Here, the length of the tip 834 protruding after penetrating through the discharge film 813 is determined according to a formation position of the stopper 852. It is preferable that the stopper 852 is formed in such a way as to restrict the protruding distance of the tip 834 so that one end portion of the tip 834 can be located inside the discharge passage 821.

As described above, after the tip 834 penetrating through the discharge film 813 is located inside the discharge passage 821, even though the reacted specimen splashes when the discharge film 813 is penetrated by the tip 834, the splashed specimen remains in the discharge passage 821 in a state where it is stained on the discharge passage 821, and hence, it prevents a loss of the reacted specimen.

Furthermore, it is preferable to form an insertion portion 818 at the other end portion of the inside of the chamber 810.

Here, it is preferable that the insertion portion 818 is gradually reduced in cross sectional area toward the discharge film 813.

Accordingly, when the tip 834 moves toward the discharge film 813, the tip 834 is effectively guided to the discharge film 813 while sliding in a state where it is in contact with the insertion portion 818.

Meanwhile, as shown in FIG. 25, the stopper 852 makes the tip 834 be inserted into the specimen to a constant depth even while the specimen 871 is extracted by the specimen extracting portion 831.

In other words, when the tip 834 is inserted through the opening portion 872 of the tube 870 filled with the specimen 871 to be extracted, the stopper 852 is inserted no more because being caught to the opening portion 872, so that just a predetermined portion of the tip 834 can be inserted into the specimen 871.

Furthermore, the specimen 871 is introduced into the specimen extracting portion 831 by the capillary force.

Therefore, the sampler according to the present invention can extract the specimen in stability and uniformly manage the volume of the specimen accommodated in the specimen extracting portion 831.

As shown in FIG. 24(*c*), in a state where one end portion of the tip 834 is located inside the discharge passage 821, when the pressing plate 825 formed on the outer face of the chamber 810 is pressed, the inside pressure of the chamber 810 rises.

In this instance, because the other end portion of the inside of the chamber 810 is sealed by the pressurizing portion 853, the mixed specimen is discharged through the opened discharge passage 821.

Here, because both sides and one end portion of the specimen extracting portion 831 are opened toward the outside of the tip 834, the tip 834 stops the discharge passage 821 so as to prevent the reacted specimen from being discharged.

In this instance, the pressing portion 825 may be formed integrally with the outer face of the chamber 810, and more concretely, the pressing portion 825 may be a part of the chamber 810.

Therefore, it is preferable that the chamber 810 is made of a material with a deformable intensity to the extent that the pressing portion 825 and the outer face of the chamber 810 can be pressed by an external force.

The pressing portion 825 can be pressed by the user's hand and is properly pressed according to thickness of the tip 834 inserted into the chamber 810.

Additionally, it is preferable that the chamber 810 is made of a transparent material so that the user can see the tip 834, the movable bar 830 and the reacted specimen located inside the chamber 810 with the naked eyes.

In the meantime, the reacted specimen is drippily discharged from the discharge part 820 when the pressing portion 825 is pressed.

For this, it is preferable that the discharge passage 821 is formed to have a diameter suitable for kinds of the reacted specimens so that the reacted specimen is drippily discharged.

Moreover, it is preferable that the discharge part 820 is detachably joined to the chamber 810.

Accordingly, the discharge part 820 can be replaced with a discharge part which has a discharge passage 821 suitable for the kind and the discharged volume of the reacted specimen.

Furthermore, the volume of a drop of the reacted specimen discharged may be varied according to the size of the discharge part 820, and can be regulated according to a diameter of the discharge passage 821.

Figure 26:
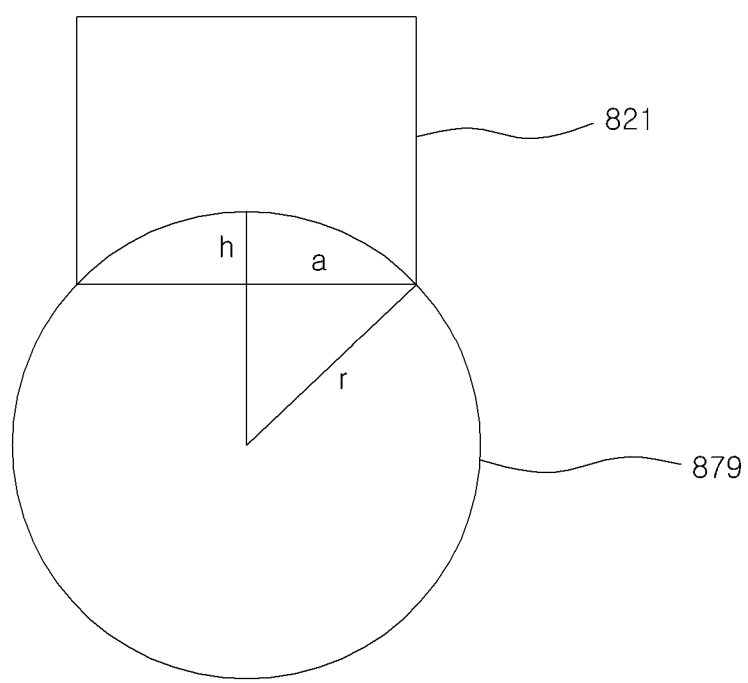
FIG. 26 is an exemplary view showing how to find a diameter of a discharge path of the sampler according to the fifth preferred embodiment.

FIG. 26 is an exemplary view showing how to find a diameter of a discharge path of the sampler according to the fifth preferred embodiment.

As shown in FIG. 26, it is preferable that the discharge passage 821 has a diameter corresponding to kinds and the discharged volume of the reacted specimen in the inside space of the chamber 810.

For this, the diameter of the discharge passage 821 can be obtained using a size of a spherical cap.

For instance, in the case that the radius of the discharge passage 821 is a, a radius of the reacted specimen drop 879 is r, and a height of the spherical cap is h, the volume (V) of the reacted specimen drop 879 is $V=4/3\pi r^3$, and the diameter of the discharge passage 821 can be obtained through the formula, $r=(a^2+h^2)/2h$.

Additionally, the diameter of the discharge passage 821 can be obtained using a surface tension of the reacted specimen drop 879.

For instance, the diameter of the discharge passage 821 can be obtained through the formula, $W=2\pi r\gamma$, wherein W=weight of reacted specimen drop, r=radius of discharge passage, and $\gamma$=surface tension.

In the meantime, in order to check whether or not it is possible to extract the specimen of the fixed quantity and quantitatively discharge the sample using the sampler according to the present invention, the following test was carried out.

Specimen: Whole blood
Buffer: Sample dilution buffer
How to test
1. Put the tip in a blood tube and extract a specimen of the fixed quantity.
2. Fit the tip into the chamber, shake the chamber to dilute the specimen, and press the chamber to discharge the diluted buffer.

Test result
1. Volume (ug) absorbed to the specimen extracting portion

| | Weight | |
| --- | --- | --- |
| | PMMA | PS |
| 1 | 13.4 | 12.8 |
| 2 | 13.3 | 14.5 |
| 3 | 14.7 | 13.4 |
| 4 | 11.7 | 14.6 |
| 5 | 12.9 | 14.7 |
| 6 | 11.4 | 12.5 |
| 7 | 12.7 | 11.6 |
| 8 | 13.9 | 11.7 |
| 9 | 12.8 | 11.7 |
| Avg | 12.97778 | 13.0555556 |
| STDEV | 1.02 | 1.30 |

It was confirmed that specimens were extracted by the same tips, the volumes of the specimens extracted into the specimen extracting portions of the tips were on a similar level.

2. Discharged weight (ug) (Buffer Vol. 600 ul (=tip vol 12 ug*50 times dilution)

| | ug | Weight of $2^{nd}$ drop (ug) |
| --- | --- | --- |
| 1 | 27.6 | 34.4 |
| 2 | 28.3 | 26.5 |
| 3 | 29.4 | 34.9 |
| 4 | 31.2 | 30.2 |
| 5 | 33.9 | 16.8 |
| 6 | 33 | 21.2 |
| 7 | 26.4 | 25.5 |
| 8 | 29.5 | 27.7 |
| 9 | 30.5 | 32.2 |
| 10 | 36.5 | 34.6 |
| Avg | 30.63 | 28.4 |
| STDEV | 3.10 | 6.09 |

It was confirmed that volumes of buffers discharged from the samplers were on a similar level when the samples were diluted at the same rate.

Figure 27:
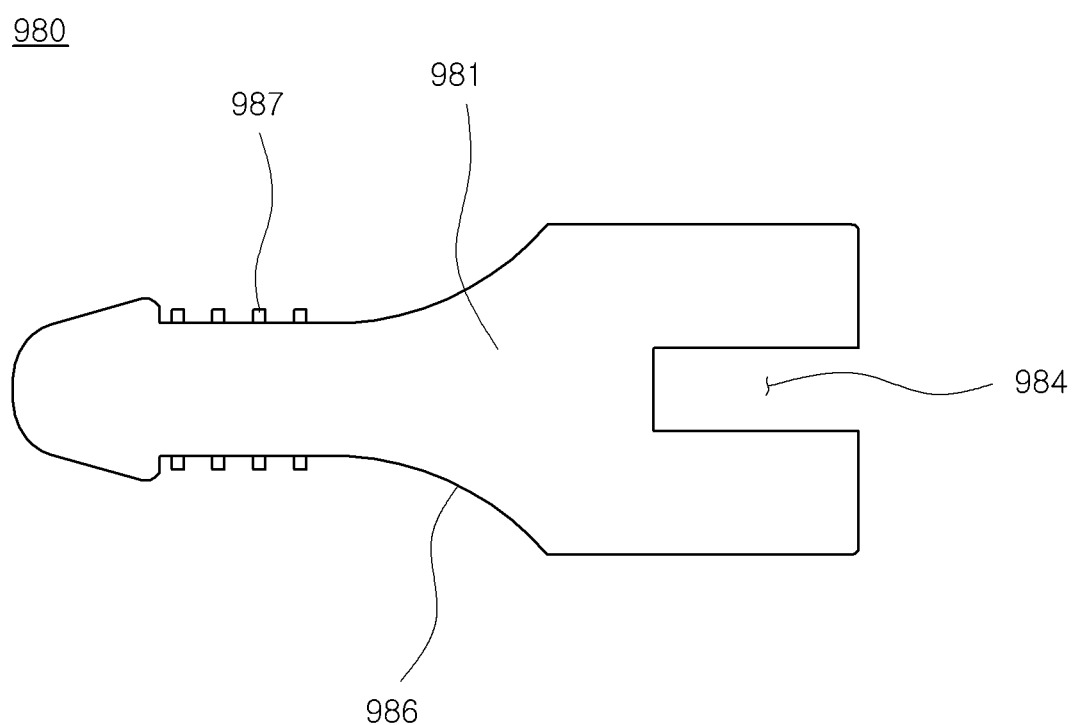
FIG. 27 is a plan view of a cap applied to a sampler according to a sixth preferred embodiment of the present invention.
Figure 28:
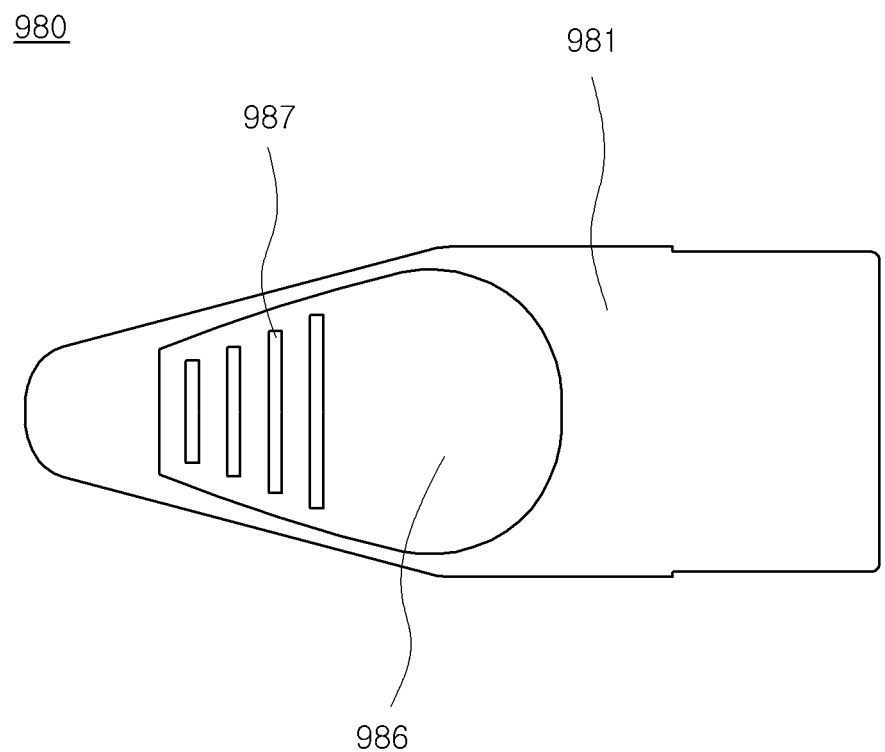
FIG. 28 is a front view of the cap applied to the sampler.
Figure 29:
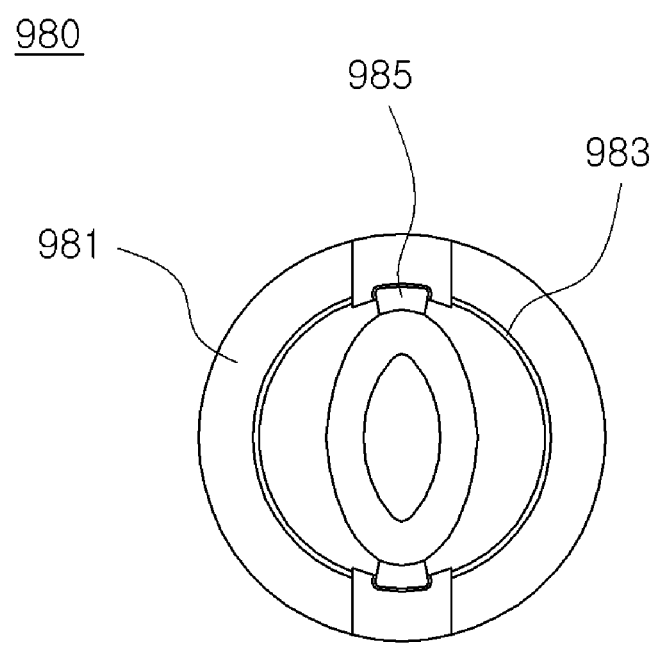
FIG. 29 is a right side view of the cap applied to the sampler.
Figure 30:
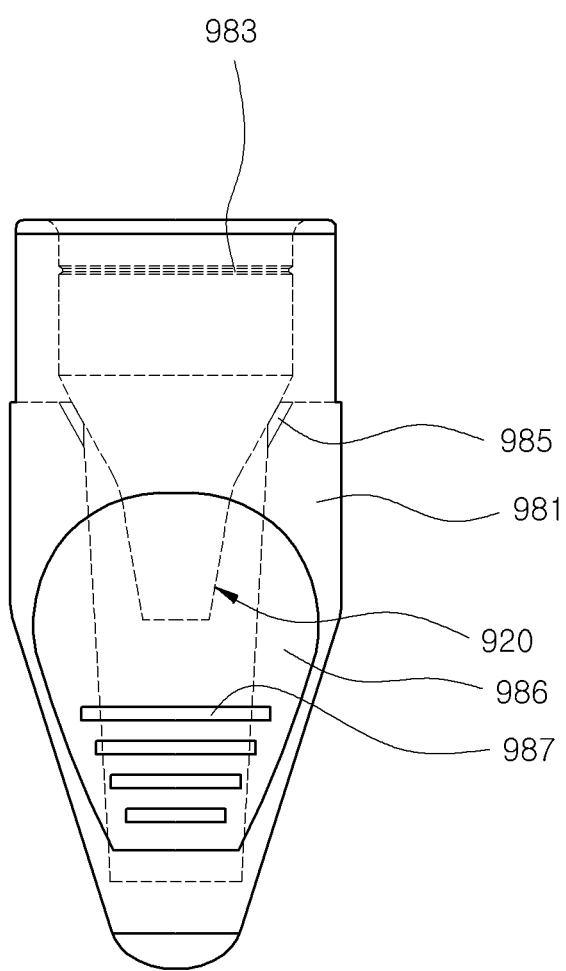
FIG. 30 is a partial view showing a state where the cap is joined to the chamber of the sampler according to the sixth preferred embodiment of the present invention.
Figure 31:
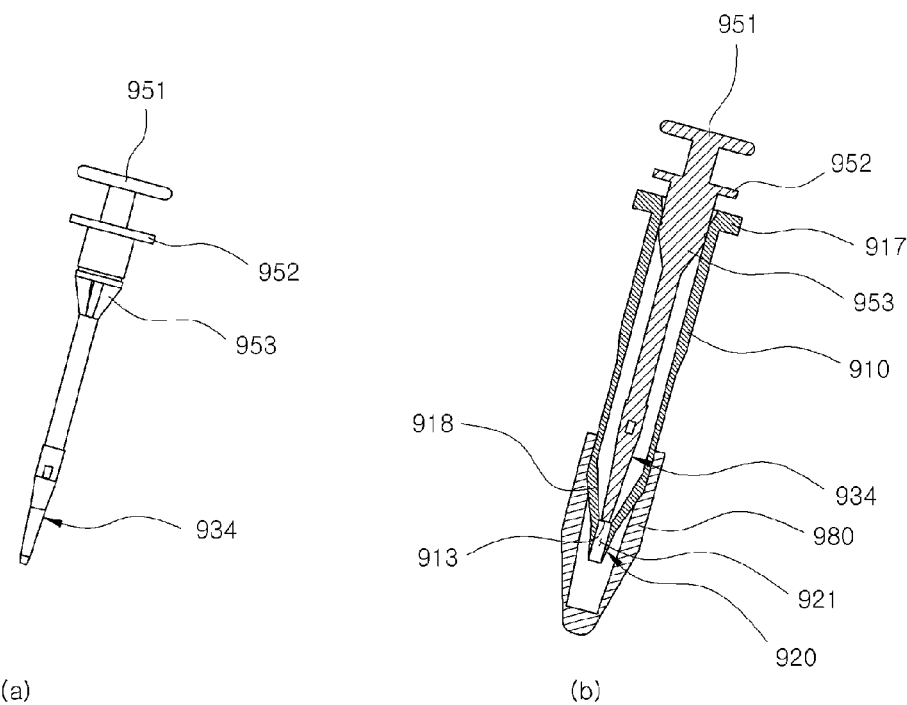
FIG. 31 is a sectional view showing an operational state in the case that the cap is applied to the sampler.
Figure 31:
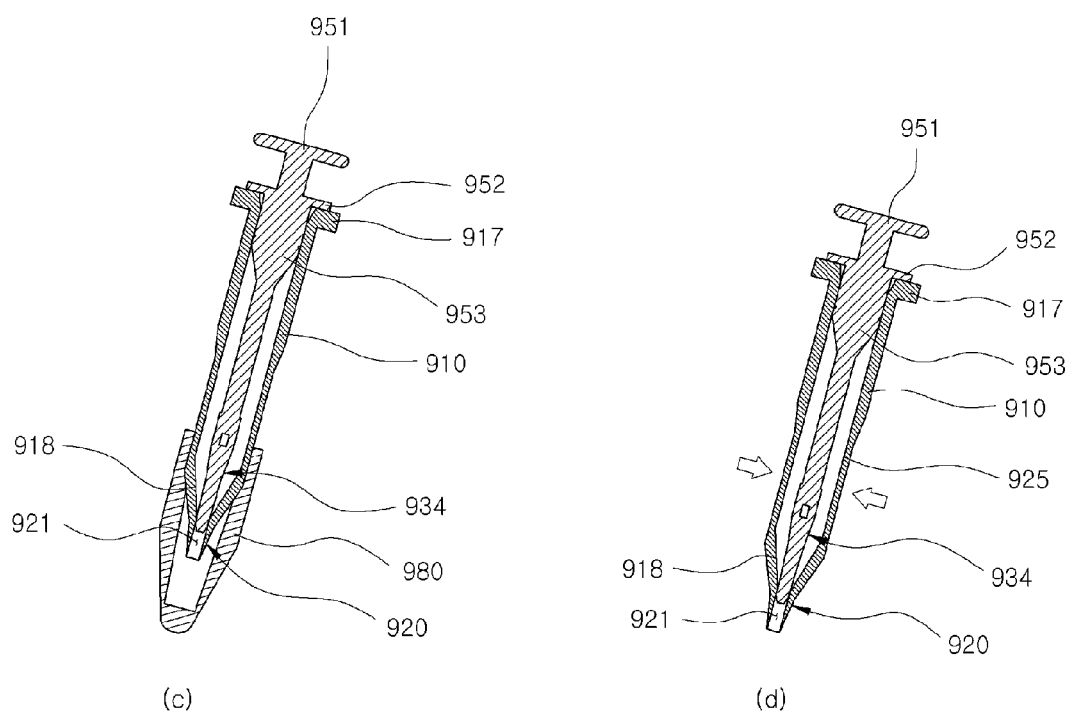

FIG. 27 is a plan view of a cap applied to a sampler according to a sixth preferred embodiment of the present invention, FIG. 28 is a front view of the cap applied to the sampler, FIG. 29 is a right side view of the cap applied to the sampler, FIG. 30 is a partial view showing a state where the cap is joined to the chamber of the sampler according to the sixth preferred embodiment of the present invention, and FIG. 31 is a sectional view showing an operational state in the case that the cap is applied to the sampler.

Referring to FIGS. 27 to 31, the sampler according to the sixth preferred embodiment of the present invention further includes a cap 980 joined to the other end of the chamber 910 for accommodating the reacted specimen leaking due to the inside pressure of the chamber 910 when the other end of the chamber 910 is perforated.

When the tip 934 penetrates through a discharge film 913 of the chamber 910, some of the reacted specimen leaks out between the tip 934 and the discharge film 913. Therefore, in order to prevent a leakage of the reacted specimen, after the cap 980 accommodates the leaking specimen therein, the cap 980 is removed together with the leaked specimen, and then, the quantitative discharge work is carried out. Accordingly, the sampler according to the sixth preferred embodiment can keep an experiment environment clean.

Of course, as described above, even though the cap 980 is applied, because the inside pressure of the chamber 910 and the dilution ratio of the diluted solution are not changed, it does not have any influence on the quantitative discharge.

Based on the sampler illustrated in FIGS. 21 to 26, the case that the cap 980 is applied is described, but of course, the cap 980 can be applied to the samplers according to all the described embodiments in the same way.

The cap 980 has a body 981 which is opened in one side and has an inside space. It is preferable that the body 981 is made of an elastic material so that the other end of the chamber 910 can be smoothly inserted into the cap 980 when the chamber 910 is joined to the cap 980 and can keep a joining force after the chamber 910 is inserted into the cap 980.

Moreover, the body 981 has a cut portion 984 disposed at a portion which is joined with the chamber 910 so as to disperse pressure applied to the cap 980 when the chamber 910 is joined with the cap 980.

The cap 980 further includes at least one protrusion 983 formed at one side of the inner circumference thereof in the circumferential direction, so that the chamber 910 and the cap 980 can be forcedly fit with each other.

Except the portion where the cut portion 984 is formed, the protrusion 983 is inwardly formed in a ring shape so as to keep the joining force after the chamber 910 is inserted into the cap 980.

Meanwhile, the cap 980 may further include at least one pressure discharge hole 985 for decreasing pressure generated when the cap 980 is joined with the chamber.

As shown in FIGS. 29 and 30, the pressure discharge hole 985 has predetermined width and length along all sides of the inside of the body 981. When the discharge part 920 of the chamber 910 is inserted, a passage is formed between the outer face of the discharge part 920 and the inner face of the cap 980.

The pressure discharge hole 985 discharges the inside pressure of the chamber 910 generated when the chamber is inserted so as to prevent the cap 980 from being separated from the chamber 910 by pressure and to prevent the specimen inside the chamber 910 from additionally leaking out by the inside pressure of the cap 980. Furthermore, the cap 980 includes: a hand-grip part 986 allowing the user to grasp with the hand when the cap 980 is joined to or separated from the chamber 910; and at least one slip-preventing protrusion 987 formed at the hand-grip part 986 for preventing a slip.

Now, referring to FIG. 31, an operation state of the cap 980 which is applied to the sampler according to the present invention will be described as follows.

First, extract a specimen using the tip 934 (*a*), and then, insert and push the tip 934 into the chamber 910 before the tip 934 reaches the discharge film 913 in a state where the cap 980 is covered to the discharge part 920 of the chamber 910, and then, shake the sampler to mix the specimen and the buffer (b).

Additionally, when the user presses the pressing plate 951 to push the tip 934 more, the discharge film 913 is perforated and the end of the tip 934 is located at the discharge passage 921. In this instance, when the tip 934 perforates the discharge film 913, a small amount of the solution leaking out between the tip 934 and the discharge film 913 is accommodated in the cap 980 (*c*).

After that, the user removes the cap 980 joined with the chamber 910 and presses the pressing portion 925 of the chamber 910 so as to quantitatively discharge the reacted specimen accommodated in the chamber 910 through the inside passage of the tip 934 and the discharge passage 921 (*d*).

The sampler according to the present invention can obtain the specimen of the fixed quantity using the capillary structure, and can quantitatively discharge the reacted specimen by mixing the previously measured reagent and the specimen.

Moreover, the sampler according to the present invention can mix the previously measured reagent with the specimen at a certain ratio and at a certain concentration without other external measuring devices and external power, can be assembled in an one-touch manner, carry out all processes just by one-direction manipulation without using many steps or two-way manipulation, and prevent the preprocessed sample from leaking out during the quantitative discharge process so as to keep an experimental environment clean.

As described above, while the present invention has been particularly shown and described with reference to the example embodiments thereof, it will be understood by those of ordinary skill in the art that the above embodiments of the present invention are all exemplified and various changes, modifications and modifications may be made therein without departing from the essential characteristics and scope of the present invention described in claims. Therefore, if the changed or modified embodiments basically include the components of the present invention described in claims, all of the embodiments belong to the technical scope of the present invention.

What is claimed is:

1. A sampler comprising:
   a tip having a specimen extracting portion formed at an end portion of the tip for accommodating an extracted specimen therein; and
   a single chamber having a penetrable pouch disposed at a first end of the chamber, a penetrable discharge film formed at a second end of the chamber so as to accommodate a reagent inside the chamber,
   wherein the reagent and the specimen are mixed together in the chamber so as to form a reacted specimen in the chamber while the end portion of the tip firstly penetrates through the pouch and is inserted into the chamber when the tip moves in a first direction, and the reacted specimen is quantitatively discharged out from the chamber through the second end of the chamber while the end portion of the tip secondly penetrates through the discharge film when the tip further moves in the first direction, and
   wherein the chamber further includes a pressing portion that is formed with a deformable material, and the reacted specimen is discharged from the chamber based on a pressing of an outer surface of the pressing portion.

2. The sampler according to claim 1, further comprising:
   a discharge part being disposed at the second end of the chamber and having a discharge passage formed therein for quantitatively discharging the reacted specimen when the pressing portion is pressed in a state where the tip penetrating the discharge film is located in the discharge passage.

3. The sampler according to claim 2, wherein the discharge part is detachably joined to the second end of the chamber and is replaceable with a discharge part, which has a diameter of a discharge passage corresponding to a discharged volume of the reacted specimen.

4. The sampler according to claim 2, wherein the tip comprises a movable bar formed integrally, and the movable bar comprises:
   a pressing plate to which an external force applied to make the tip penetrate through the discharge film is applied;
   a stopper caught to the second end of the chamber so as to stop a movement of the movable bar; and
   a pressurizing portion being moved in a state where an outer face thereof is in contact with an inner face of the chamber when the movable bar is moved, so that one side of the inside of the chamber is sealed and the reacted specimen pressurized by the pressing portion is discharged to the discharge part.

5. The sampler according to claim 1, wherein the pressing portion is formed integrally with an outer face of the chamber in such a way as to be pressed by an external force so as to increase the pressure at the side of the chamber.

6. The sampler according to claim 1, further comprising:
   a cap joined to the second end of the chamber for accommodating the reacted specimen leaking out by an inside pressure of the chamber when the tip moves to the second distance and the discharge film at the second end of the chamber is penetrated by the tip.

7. The sampler according to claim 6, wherein the cap comprises at least one pressure discharge hole for decreasing pressure generated when the cap is joined with the chamber.

8. The sampler according to claim 1, further comprising:
   a cap joined to the second end of the chamber for accommodating the reacted specimen leaking out by an inside pressure of the chamber when a film at the second end of the chamber is penetrated by the tip.

* * * * *